US010456459B2

(12) United States Patent
Dominowski et al.

(10) Patent No.: US 10,456,459 B2
(45) Date of Patent: Oct. 29, 2019

(54) LIPOSOMAL ADJUVANT COMPOSITIONS

(71) Applicant: Zoetis Services LLC, Florham Park, NJ (US)

(72) Inventors: Paul Joseph Dominowski, Kalamazoo, MI (US); Duncan Mwangi, Portage, MI (US); Sharath K. Rai, Portage, MI (US); Dennis L. Foss, Mattawan, MI (US); Traci K. Godbee, Climax, MI (US); Laurel Mary Sly, Portage, MI (US); Suman Mahan, Kalamazoo, MI (US); Shaunak Vora, Portage, MI (US)

(73) Assignee: Zoetis Services LLC, Parsippany, NJ (US)

(*) Notice: Subject to any disclaimer, the term of this patent is extended or adjusted under 35 U.S.C. 154(b) by 0 days.

(21) Appl. No.: 15/213,627

(22) Filed: Jul. 19, 2016

(65) Prior Publication Data

US 2018/0021424 A1 Jan. 25, 2018

Related U.S. Application Data

(60) Provisional application No. 62/194,355, filed on Jul. 20, 2015.

(51) Int. Cl.
*A61K 39/12* (2006.01)
*A61K 39/39* (2006.01)
*A61K 39/145* (2006.01)
*C12N 7/00* (2006.01)
*A61K 39/012* (2006.01)
*A61K 39/00* (2006.01)

(52) U.S. Cl.
CPC ............ *A61K 39/12* (2013.01); *A61K 39/012* (2013.01); *A61K 39/39* (2013.01); *C12N 7/00* (2013.01); *A61K 2039/5252* (2013.01); *A61K 2039/552* (2013.01); *A61K 2039/55555* (2013.01); *A61K 2039/55561* (2013.01); *A61K 2039/70* (2013.01); *C12N 2710/16734* (2013.01); *C12N 2710/16771* (2013.01); *C12N 2760/16134* (2013.01); *C12N 2760/16171* (2013.01); *C12N 2770/24034* (2013.01); *C12N 2770/24334* (2013.01); *C12N 2770/24371* (2013.01)

(58) Field of Classification Search
CPC ...... A61K 2039/5252; A61K 2039/552; A61K 2039/55555; A61K 2039/55561; A61K 2039/70; A61K 39/012; A61K 39/12; A61K 39/39; C12N 2710/16734; C12N 2710/16771; C12N 2760/16134; C12N 2760/16171; C12N 2770/24034; C12N 2770/24334; C12N 2770/24371; C12N 7/00
USPC .......................................................... 424/50
See application file for complete search history.

(56) References Cited

U.S. PATENT DOCUMENTS

| 4,855,283 | A | * | 8/1989 | Lockhoff | ............... | A61K 39/39 |
| | | | | | | 424/278.1 |
| 7,049,302 | B1 | | 5/2006 | Kensil | | |
| 8,580,280 | B2 | * | 11/2013 | Dominowski | ..... | A61K 39/0011 |
| | | | | | | 424/278.1 |
| 2006/0008519 | A1 | * | 1/2006 | Davidsen | ............ | A61K 9/1272 |
| | | | | | | 424/450 |
| 2006/0140875 | A1 | * | 6/2006 | Krieg | ................... | A61K 9/0043 |
| | | | | | | 424/46 |
| 2008/0254065 | A1 | | 10/2008 | Podda et al. | | |
| 2009/0324641 | A1 | | 12/2009 | Dominowski et al. | | |
| 2010/0166780 | A1 | | 7/2010 | Debelak et al. | | |
| 2013/0084306 | A1 | * | 4/2013 | Davis | ................... | A61K 39/099 |
| | | | | | | 424/196.11 |
| 2015/0140034 | A1 | * | 5/2015 | Dominowski | ....... | A61K 39/002 |
| | | | | | | 424/203.1 |

FOREIGN PATENT DOCUMENTS

| WO | WO-9848836 A1 * | 11/1998 | ........... A61K 39/105 |
| WO | 2003/028760 | 4/2003 | |
| WO | 2005/039634 | 5/2005 | |
| WO | 2009/156960 | 12/2009 | |
| WO | WO-2014186291 A1 * | 11/2014 | ............. A61K 39/12 |
| WO | WO-2015042369 A2 * | 3/2015 | ........... A61K 39/002 |

OTHER PUBLICATIONS

Manesis et al. Febs Letters, 1979, vol. 102, No. 1, pp. 107-111. (Year: 1979).*
Lechmann et al., "Hepatitis C Virus-Like Particles Induce Virus-Specific Humoral and Cellular Immune Responses in Mice", Hepatology, 34:417-423, 2001.
PCT International Search Report, PCT/IB2011/052347, dated Oct. 7, 2011 (5 pages).
Mahmoud R. Jaafari, "The role of CpG ODN in enhancement of immune response and protection in BALB/c mice immunized with recombinant major surface glycoprotein of Leishmania (rgp63) encapsulated in cationic lip," Vaccine 25 (2007) pp. 6107-6117.
D. Davis & G. Gregoriadis, "Liposomes as adjuvants with immunopurified tetanus toxoid: influence of liposomal characteristics," Immunology 1987 61, pp. 229-234.
Duncan E. S. Stewart-Tull, "Adjuvant Formulations for Experimental Vaccines," Methods in Molecular Medicine, vol. 87: Vaccine Protocols, 2nd ed., pp. 175-193.
Hassan Farhood, et al. "Cationic Liposomes for Direct Gene Transfer in Therapy of Cancer and Other Diseases," Annals New York Academy of Sciences, pp. 23-35.
Christopher Kirby, et al. "Effect of the Cholesterol Content of Small Unilamellar Liposomes on their Stability in vivo and in vitro," Biochem. J. (1980) 186, pp. 591-598.
Jean M. Muderhwa et al., "Oil-in-Water Liposomal Emulsions: Characterization and Potential Use in Vaccine Delivery," Journal of Pharmaceutical Sciences, vol. 88, No. 12, Dec. 1999, pp. 1332-1339.
Neeland, M.R., et al., "Incorporation of CpG into a Liposomal Vaccine Formulation Increases the Maturation of Antigen-Loaded Dendritic Cells and Monocytes to Improve Local and Systemic Immunity," The Journal of Immunology, 2014, vol. 192, pp. 3666-3675.

* cited by examiner

*Primary Examiner* — Janet L Epps-Smith
(74) *Attorney, Agent, or Firm* — Vyacheslav Vasilyev

(57) ABSTRACT

The invention provides a liposomal adjuvant composition comprising an external membrane and an internal compartment, the external membrane comprising: a quaternary ammonium compound; a sterol; a phospholipid; and a glycolipid. Vaccine compositions comprising the liposomal adjuvant of the instant invention are also provided.

25 Claims, No Drawings
Specification includes a Sequence Listing.

SEQUENCE LISTING

<160> NUMBER OF SEQ ID NOS: 136

<210> SEQ ID NO 1
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 1
tcgtcgacga tcggcgcgcg ccg 23

<210> SEQ ID NO 2
<211> LENGTH: 23
<212> TYPE: DNA
<213> ORGANISM: Artificial sequence
<220> FEATURE:
<223> OTHER INFORMATION: CpG oligonucleotide

<400> SEQUENCE: 2
tcgacgtcga tcggcgcgcg ccg 23

<210> SEQ ID NO 3
<211> LENGTH: 24
<212> TYPE: DNA
<213> ORGANISM: Artificial Sequence
<220> FEATURE:
<223> OTHER INFORMATION: CpG oligonucleotide

```
<400> SEQUENCE: 3
tcgacgtcga tcggcgcgcg ccgt                                              24

<210> SEQ ID NO 4
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 4
ncgacgtcga tcggcgcgcg ccg                                               23

<210> SEQ ID NO 5
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 5
ncgacgtcga tcggcgcgcg ccgt                                              24

<210> SEQ ID NO 6
<211> LENGTH: 24
<212> TYPE: DNA
<213> ORGANISM: Artificial Sequence
<220> FEATURE:
<223> OTHER INFORMATION: CpG Oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 6
ncgacgtcga tcggcgcgcg ccgt                                              24

<210> SEQ ID NO 7
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Ethyl-2'-deoxyuridine

<400> SEQUENCE: 7
ncgacgtcga tcggcgcgcg ccg                                               23

<210> SEQ ID NO 8
<211> LENGTH: 24
<212> TYPE: DNA
<213> ORGANISM: Artificial Sequence
<220> FEATURE:
<223> OTHER INFORMATION: CpG Oligonucleotide
<220> FEATURE:
<221> NAME/KEY: misc_feature
<222> LOCATION: (1)..(1)
<223> OTHER INFORMATION: 5'-Iodo-2'-deoxyuridine
```

```
<400> SEQUENCE: 8
ncgtcgacga tcggcggccg ccgt                                          24

<210> SEQ ID NO 9
<211> LENGTH: 24
<212> TYPE: DNA
<213> ORGANISM: Artificial Sequence
<220> FEATURE:
<223> OTHER INFORMATION: CpG Oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 9
ncgtcgacga tcggcggccg ccgt                                          24

<210> SEQ ID NO 10
<211> LENGTH: 23
<212> TYPE: DNA
<213> ORGANISM: Artificial Sequence
<220> FEATURE:
<223> OTHER INFORMATION: CpG Oligonucleotide

<400> SEQUENCE: 10
tcgtcgacga tcggcgcgcg ccg                                           23

<210> SEQ ID NO 11
<211> LENGTH: 20
<212> TYPE: RNA
<213> ORGANISM: Artificial Sequence
<220> FEATURE:
<223> OTHER INFORMATION: immunostimulatory oligoribonucleotide

<400> SEQUENCE: 11
uuguuguugu uguuguuguu                                               20

<210> SEQ ID NO 12
<211> LENGTH: 20
<212> TYPE: RNA
<213> ORGANISM: Artificial Sequence
<220> FEATURE:
<223> OTHER INFORMATION: Immunostimulatory oligoribonucleotide

<400> SEQUENCE: 12
uuauuauuau uauuauuauu                                               20

<210> SEQ ID NO 13
<211> LENGTH: 19
<212> TYPE: RNA
<213> ORGANISM: Artificial Sequence
<220> FEATURE:
<223> OTHER INFORMATION: Immunostimulatory oligoribonucleotide

<400> SEQUENCE: 13
aaacgcucag ccaaagcag                                                19

<210> SEQ ID NO 14
<211> LENGTH: 21
<212> TYPE: DNA
<213> ORGANISM: Artificial Sequence
<220> FEATURE:
<223> OTHER INFORMATION: DNA/RNA hybrid
<220> FEATURE:
<221> NAME/KEY: misc_feature
<222> LOCATION: (11)..(17)
<223> OTHER INFORMATION: ribonucleotides
```

<400> SEQUENCE: 14
tcgtcgtttt guuguguttt t                     21

<210> SEQ ID NO 15
<211> LENGTH: 16
<212> TYPE: PRT
<213> ORGANISM: Artificial Sequence
<220> FEATURE:
<223> OTHER INFORMATION: Fragment of Swine Influenza Virus NP protein

<400> SEQUENCE: 15

Met Ala Thr Gln Gly Thr Lys Arg Ser Tyr Glu Gln Met Glu Thr Gly
1               5                   10                  15

<210> SEQ ID NO 16
<211> LENGTH: 16
<212> TYPE: PRT
<213> ORGANISM: Artificial sequence
<220> FEATURE:
<223> OTHER INFORMATION: Fragment of NP protein of Swine Influenza Virus

<400> SEQUENCE: 16

Gly Thr Lys Arg Ser Tyr Glu Gln Met Glu Thr Gly Gly Glu Arg Gln
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Fragment of Swine Influenza Virus NP protein

<400> SEQUENCE: 17

Ser Tyr Glu Gln Met Glu Thr Gly Gly Glu Arg Gln Asp Ala Thr Glu
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 18

Met Glu Thr Gly Gly Glu Arg Gln Asp Ala Thr Glu Ile Lys Ala Ser
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 19

Gly Glu Arg Gln Asp Ala Thr Glu Ile Lys Ala Ser Val Gly Arg Met
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Fragment of NP protein of Swine Influenza Virus

```
<400> SEQUENCE: 20

Asp Ala Thr Glu Ile Lys Ala Ser Val Gly Arg Met Val Gly Gly Ile
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 21

Ile Lys Ala Ser Val Gly Arg Met Val Gly Gly Ile Gly Arg Phe Tyr
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 22

Val Gly Arg Met Val Gly Gly Ile Gly Arg Phe Tyr Ile Gln Met Cys
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 23

Val Gly Gly Ile Gly Arg Phe Tyr Ile Gln Met Cys Thr Glu Leu Lys
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 24

Gly Arg Phe Tyr Ile Gln Met Cys Thr Glu Leu Lys Leu Ser Asp Tyr
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 25

Ile Gln Met Cys Thr Glu Leu Lys Leu Ser Asp Tyr Glu Gly Arg Leu
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

```
<400> SEQUENCE: 26

Thr Glu Leu Lys Leu Ser Asp Tyr Glu Gly Arg Leu Ile Gln Asn Ser
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 27

Leu Ser Asp Tyr Glu Gly Arg Leu Ile Gln Asn Ser Ile Thr Ile Glu
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 28

Glu Gly Arg Leu Ile Gln Asn Ser Ile Thr Ile Glu Arg Met Val Leu
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 29

Ile Gln Asn Ser Ile Thr Ile Glu Arg Met Val Leu Ser Ala Phe Asp
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 30

Ile Thr Ile Glu Arg Met Val Leu Ser Ala Phe Asp Glu Arg Arg Asn
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 31

Arg Met Val Leu Ser Ala Phe Asp Glu Arg Arg Asn Lys Tyr Leu Glu
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

<400> SEQUENCE: 32

Ser Ala Phe Asp Glu Arg Arg Asn Lys Tyr Leu Glu Glu His Pro Ser
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 33

Glu Arg Arg Asn Lys Tyr Leu Glu Glu His Pro Ser Ala Gly Lys Asp
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 34

Lys Tyr Leu Glu Glu His Pro Ser Ala Gly Lys Asp Pro Lys Lys Thr
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 35

Glu His Pro Ser Ala Gly Lys Asp Pro Lys Lys Thr Gly Gly Pro Ile
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 36

Ala Gly Lys Asp Pro Lys Lys Thr Gly Gly Pro Ile Tyr Arg Arg Val
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 37

Pro Lys Lys Thr Gly Gly Pro Ile Tyr Arg Arg Val Asp Gly Lys Trp
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Fragment of NP protein of Swine Influenza Virus

```
<400> SEQUENCE: 38

Gly Gly Pro Ile Tyr Arg Arg Val Asp Gly Lys Trp Met Arg Glu Leu
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 39

Tyr Arg Arg Val Asp Gly Lys Trp Met Arg Glu Leu Ile Leu Tyr Asp
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 40

Asp Gly Lys Trp Met Arg Glu Leu Ile Leu Tyr Asp Lys Glu Glu Ile
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 41

Met Arg Glu Leu Ile Leu Tyr Asp Lys Glu Glu Ile Arg Arg Val Trp
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 42

Ile Leu Tyr Asp Lys Glu Glu Ile Arg Arg Val Trp Arg Gln Ala Asn
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 43

Lys Glu Glu Ile Arg Arg Val Trp Arg Gln Ala Asn Asn Gly Glu Asp
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

```
<400> SEQUENCE: 44

Arg Arg Val Trp Arg Gln Ala Asn Asn Gly Glu Asp Ala Thr Ala Gly
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 45

Arg Gln Ala Asn Asn Gly Glu Asp Ala Thr Ala Gly Leu Thr His Ile
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 46

Asn Gly Glu Asp Ala Thr Ala Gly Leu Thr His Ile Met Ile Trp His
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 47

Ala Thr Ala Gly Leu Thr His Ile Met Ile Trp His Ser Asn Leu Asn
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 48

Leu Thr His Ile Met Ile Trp His Ser Asn Leu Asn Asp Ala Thr Tyr
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 49

Met Ile Trp His Ser Asn Leu Asn Asp Ala Thr Tyr Gln Arg Thr Arg
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

```
<400> SEQUENCE: 50

Ser Asn Leu Asn Asp Ala Thr Tyr Gln Arg Thr Arg Ala Leu Val Arg
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 51

Asp Ala Thr Tyr Gln Arg Thr Arg Ala Leu Val Arg Thr Gly Met Asp
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 52

Gln Arg Thr Arg Ala Leu Val Arg Thr Gly Met Asp Pro Arg Met Cys
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 53

Ala Leu Val Arg Thr Gly Met Asp Pro Arg Met Cys Ser Leu Met Gln
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 54

Thr Gly Met Asp Pro Arg Met Cys Ser Leu Met Gln Gly Ser Thr Leu
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 55

Pro Arg Met Cys Ser Leu Met Gln Gly Ser Thr Leu Pro Arg Arg Ser
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

```
<400> SEQUENCE: 56

Ser Leu Met Gln Gly Ser Thr Leu Pro Arg Arg Ser Gly Ala Ala Gly
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 57

Gly Ser Thr Leu Pro Arg Arg Ser Gly Ala Ala Gly Ala Ala Val Lys
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 58

Pro Arg Arg Ser Gly Ala Ala Gly Ala Ala Val Lys Gly Val Gly Thr
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 59

Gly Ala Ala Gly Ala Ala Val Lys Gly Val Gly Thr Ile Ala Met Glu
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 60

Ala Ala Val Lys Gly Val Gly Thr Ile Ala Met Glu Leu Ile Arg Met
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 61

Gly Val Gly Thr Ile Ala Met Glu Leu Ile Arg Met Ile Lys Arg Gly
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

```
<400> SEQUENCE: 62

Ile Ala Met Glu Leu Ile Arg Met Ile Lys Arg Gly Ile Asn Asp Arg
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 63

Leu Ile Arg Met Ile Lys Arg Gly Ile Asn Asp Arg Asn Phe Trp Arg
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 64

Ile Lys Arg Gly Ile Asn Asp Arg Asn Phe Trp Arg Gly Glu Asn Gly
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 65

Ile Asn Asp Arg Asn Phe Trp Arg Gly Glu Asn Gly Arg Arg Thr Arg
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 66

Asn Phe Trp Arg Gly Glu Asn Gly Arg Arg Thr Arg Ala Ala Tyr Glu
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 67

Gly Glu Asn Gly Arg Arg Thr Arg Ala Ala Tyr Glu Arg Met Cys Asn
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

```
<400> SEQUENCE: 68

Arg Arg Thr Arg Ala Ala Tyr Glu Arg Met Cys Asn Ile Leu Lys Gly
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 69

Ala Ala Tyr Glu Arg Met Cys Asn Ile Leu Lys Gly Lys Phe Gln Thr
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 70

Arg Met Cys Asn Ile Leu Lys Gly Lys Phe Gln Thr Ala Ala Gln Arg
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 71

Ile Leu Lys Gly Lys Phe Gln Thr Ala Ala Gln Arg Ala Met Met Asp
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 72

Lys Phe Gln Thr Ala Ala Gln Arg Ala Met Met Asp Gln Val Arg Glu
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 73

Ala Ala Gln Arg Ala Met Met Asp Gln Val Arg Glu Ser Arg Asn Pro
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

<400> SEQUENCE: 74

Ala Met Met Asp Gln Val Arg Glu Ser Arg Asn Pro Gly Asn Ala Glu
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 75

Gln Val Arg Glu Ser Arg Asn Pro Gly Asn Ala Glu Ile Glu Asp Leu
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 76

Ser Arg Asn Pro Gly Asn Ala Glu Ile Glu Asp Leu Ile Phe Leu Ala
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 77

Gly Asn Ala Glu Ile Glu Asp Leu Ile Phe Leu Ala Arg Ser Ala Leu
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 78

Ile Glu Asp Leu Ile Phe Leu Ala Arg Ser Ala Leu Val Leu Arg Gly
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 79

Ile Phe Leu Ala Arg Ser Ala Leu Val Leu Arg Gly Ser Val Ala His
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Fragment of NP protein of Swine Influenza Virus

```
<400> SEQUENCE: 80

Arg Ser Ala Leu Val Leu Arg Gly Ser Val Ala His Lys Ser Cys Leu
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 81

Val Leu Arg Gly Ser Val Ala His Lys Ser Cys Leu Pro Ala Cys Val
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 82

Ser Val Ala His Lys Ser Cys Leu Pro Ala Cys Val Tyr Gly Leu Ala
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 83

Lys Ser Cys Leu Pro Ala Cys Val Tyr Gly Leu Ala Val Ala Ser Gly
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 84

Pro Ala Cys Val Tyr Gly Leu Ala Val Ala Ser Gly His Asp Phe Glu
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 85

Tyr Gly Leu Ala Val Ala Ser Gly His Asp Phe Glu Arg Glu Gly Tyr
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

```
<400> SEQUENCE: 86

Val Ala Ser Gly His Asp Phe Glu Arg Glu Gly Tyr Ser Leu Val Gly
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 87

His Asp Phe Glu Arg Glu Gly Tyr Ser Leu Val Gly Ile Asp Pro Phe
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 88

Arg Glu Gly Tyr Ser Leu Val Gly Ile Asp Pro Phe Lys Leu Leu Gln
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 89

Ser Leu Val Gly Ile Asp Pro Phe Lys Leu Leu Gln Asn Ser Gln Val
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 90

Ile Asp Pro Phe Lys Leu Leu Gln Asn Ser Gln Val Phe Ser Leu Ile
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 91

Lys Leu Leu Gln Asn Ser Gln Val Phe Ser Leu Ile Arg Pro Asn Glu
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

<400> SEQUENCE: 92

Asn Ser Gln Val Phe Ser Leu Ile Arg Pro Asn Glu Asn Pro Ala His
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 93

Phe Ser Leu Ile Arg Pro Asn Glu Asn Pro Ala His Lys Ser Gln Leu
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 94

Arg Pro Asn Glu Asn Pro Ala His Lys Ser Gln Leu Val Trp Met Ala
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 95

Asn Pro Ala His Lys Ser Gln Leu Val Trp Met Ala Cys His Ser Ala
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 96

Lys Ser Gln Leu Val Trp Met Ala Cys His Ser Ala Ala Phe Glu Asp
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 97

Val Trp Met Ala Cys His Ser Ala Ala Phe Glu Asp Leu Arg Val Ser
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Fragment of NP protein of Swine Influenza Virus

```
<400> SEQUENCE: 98

Cys His Ser Ala Ala Phe Glu Asp Leu Arg Val Ser Ser Phe Ile Arg
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 99

Ala Phe Glu Asp Leu Arg Val Ser Ser Phe Ile Arg Gly Lys Lys Val
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 100

Leu Arg Val Ser Ser Phe Ile Arg Gly Lys Lys Val Ile Pro Arg Gly
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 101

Ser Phe Ile Arg Gly Lys Lys Val Ile Pro Arg Gly Lys Leu Ser Thr
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 102

Gly Lys Lys Val Ile Pro Arg Gly Lys Leu Ser Thr Arg Gly Val Gln
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 103

Ile Pro Arg Gly Lys Leu Ser Thr Arg Gly Val Gln Ile Ala Ser Asn
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

-continued

<400> SEQUENCE: 104

Lys Leu Ser Thr Arg Gly Val Gln Ile Ala Ser Asn Glu Asn Val Glu
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 105

Arg Gly Val Gln Ile Ala Ser Asn Glu Asn Val Glu Ala Met Asp Ser
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 106

Ile Ala Ser Asn Glu Asn Val Glu Ala Met Asp Ser Asn Thr Leu Glu
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 107

Glu Asn Val Glu Ala Met Asp Ser Asn Thr Leu Glu Leu Arg Ser Arg
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 108

Ala Met Asp Ser Asn Thr Leu Glu Leu Arg Ser Arg Tyr Trp Ala Ile
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 109

Asn Thr Leu Glu Leu Arg Ser Arg Tyr Trp Ala Ile Arg Thr Arg Ser
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 110

Leu Arg Ser Arg Tyr Trp Ala Ile Arg Thr Arg Ser Gly Gly Asn Thr
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 111

Tyr Trp Ala Ile Arg Thr Arg Ser Gly Gly Asn Thr Asn Gln Gln Arg
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 112

Arg Thr Arg Ser Gly Gly Asn Thr Asn Gln Gln Arg Ala Ser Ala Gly
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 113

Gly Gly Asn Thr Asn Gln Gln Arg Ala Ser Ala Gly Gln Ile Ser Val
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 114

Asn Gln Gln Arg Ala Ser Ala Gly Gln Ile Ser Val Gln Pro Thr Phe
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 115

Ala Ser Ala Gly Gln Ile Ser Val Gln Pro Thr Phe Ser Val Gln Arg
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Fragment of NP protein of Swine Influenza Virus

```
<400> SEQUENCE: 116

Gln Ile Ser Val Gln Pro Thr Phe Ser Val Gln Arg Asn Leu Pro Phe
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 117

Gln Pro Thr Phe Ser Val Gln Arg Asn Leu Pro Phe Glu Arg Ala Thr
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 118

Ser Val Gln Arg Asn Leu Pro Phe Glu Arg Ala Thr Ile Met Ala Ala
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 119

Asn Leu Pro Phe Glu Arg Ala Thr Ile Met Ala Ala Phe Ser Gly Asn
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 120

Glu Arg Ala Thr Ile Met Ala Ala Phe Ser Gly Asn Asn Glu Gly Arg
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 121

Ile Met Ala Ala Phe Ser Gly Asn Asn Glu Gly Arg Thr Ser Asp Met
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

```
<400> SEQUENCE: 122

Phe Ser Gly Asn Asn Glu Gly Arg Thr Ser Asp Met Arg Thr Glu Val
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 123

Asn Glu Gly Arg Thr Ser Asp Met Arg Thr Glu Val Ile Arg Met Met
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 124

Thr Ser Asp Met Arg Thr Glu Val Ile Arg Met Met Glu Ser Ala Lys
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 125

Arg Thr Glu Val Ile Arg Met Met Glu Ser Ala Lys Pro Glu Asp Leu
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 126

Ile Arg Met Met Glu Ser Ala Lys Pro Glu Asp Leu Ser Phe Gln Gly
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 127

Glu Ser Ala Lys Pro Glu Asp Leu Ser Phe Gln Gly Arg Gly Val Phe
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Fragment of NP protein of Swine Influenza Virus
```

<400> SEQUENCE: 128

Pro Glu Asp Leu Ser Phe Gln Gly Arg Gly Val Phe Glu Leu Ser Asp
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 129

Ser Phe Gln Gly Arg Gly Val Phe Glu Leu Ser Asp Glu Lys Ala Thr
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 130

Arg Gly Val Phe Glu Leu Ser Asp Glu Lys Ala Thr Ser Pro Ile Val
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 131

Glu Leu Ser Asp Glu Lys Ala Thr Ser Pro Ile Val Pro Ser Phe Asp
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 132

Glu Lys Ala Thr Ser Pro Ile Val Pro Ser Phe Asp Met Ser Asn Glu
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 133

Ser Pro Ile Val Pro Ser Phe Asp Met Ser Asn Glu Gly Ser Tyr Phe
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Fragment of NP protein of Swine Influenza Virus

```
-continued

<400> SEQUENCE: 134

Pro Ser Phe Asp Met Ser Asn Glu Gly Ser Tyr Phe Phe Gly Asp Asn
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Fragment of NP protein of Swine Influenza Virus

<400> SEQUENCE: 135

Met Ser Asn Glu Gly Ser Tyr Phe Phe Gly Asp Asn Ala Glu Glu Tyr
1               5                   10                  15

<210> SEQ ID NO 136
<211> LENGTH: 14
<212> TYPE: PRT
<213> ORGANISM: Artificial Sequence
<220> FEATURE:
<223> OTHER INFORMATION: Fragment of NP protein of Swine Influenza Virus

<400> SEQUENCE: 136

Gly Ser Tyr Phe Phe Gly Asp Asn Ala Glu Glu Tyr Asp Ser
1               5                   10
```

LIPOSOMAL ADJUVANT COMPOSITIONS

CROSS-REFERENCE TO RELATED APPLICATIONS

This application claims the benefit of U.S. Provisional Application No. 62/194,355, filed on Jul. 20, 2015, the contents of which are incorporated herein by reference in their entirety.

FIELD OF THE INVENTION

This invention is in the field of vaccine adjuvants.

BACKGROUND

In the area of vaccinology, antigens are introduced into a host in a manner so as to stimulate an immune response to the antigen and therefore to the potential pathogen. The induction of an immune response depends on many factors among which are believed to be the chemical composition, characteristics and configuration of the antigen, the health and immune competence of the host, and the manner of delivery and administration of the antigen.

An immune response has many facets, some of which are exhibited by the cells of the immune system, (e.g., Dendritic cells, B-lymphocytes, T-lymphocytes, macrophages, and plasma cells). Cells of the immune system participate in the immune response through interaction with antigens or other cells of the immune system, the release of cytokines and reactivity to those cytokines. Adaptive (acquired) immune response is conveniently (but arbitrarily) divided into two main categories—humoral and cell-mediated. The humoral component of the immune response includes production of antibodies specific for the antigen. The cell-mediated component includes the generation of delayed-type hypersensitivity and cytotoxic effector T-cells specific to the antigen.

Adjuvants are substances used to potentiate an immune response when used in conjunction with the antigen. The use of an adjuvant in a vaccination protocol may, for example, elicit an immune response that is faster or greater than would be elicited with antigen alone. In addition, adjuvants may be used to direct the immune response to specific immunological pathways and to serve as a delivery vehicle for the antigen.

Liposomes and liposomal formulations are examples of adjuvants. Typically liposomes can be loaded with the antigen(s) and/or other immunomodulatory compounds, or the liposomes themselves may serve as standalone adjuvants. The antigens and/or other immunostimulatory compounds may be encapsulated in the interior of the liposome, and/or they can be attached to the liposome or incorporated into the lipid bilayer.

The factors influencing the suitability of a given liposome as a delivery vehicle in a given system presentation remain unclear. Thus there is still a need for delivery vehicles, which provide an improved efficacy. Such an improved delivery is particular for the administration of molecules which stimulate and/or elicit an immune response, for example, antigens and immunomodulators.

SUMMARY OF INVENTION

The instant invention is directed to adjuvants for enhancing the performance of a vaccine.

In certain aspects the invention provides a liposome comprising an external lipid bilayer membrane and an internal compartment, the external lipid bilayer membrane comprising: a quaternary ammonium compound; a sterol; a phospholipid; and a glycolipid of Formula I:

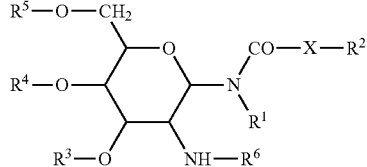

Formula I wherein, $R^1$ and $R^2$ are independently hydrogen, or a saturated alkyl radical having up to 20 carbon atoms; X is —$CH_2$—, —O— or —NH—; $R^2$ is hydrogen, or a saturated or unsaturated alkyl radical having up to 20 carbon atoms; $R^3$, $R^4$, and $R^5$ are independently hydrogen, —$SO_4^{2-}$, —$PO_4^{2-}$, —$COC_{1-10}$ alkyl; $R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers.

In certain embodiments, the quaternary ammonium compound is DDA, the sterol is cholesterol, the phospholipid is lecithin, and the glycolipid is N-(2-Deoxy-2-L-leucylamino-β-D-glucopyranosyl)-N-octadecyldodecanoylamide or an acetate thereof.

In certain embodiments, the liposome is essentially saponin-free.

In certain embodiments, the liposome further comprises an immunostimulatory oligonucleotide selected from the group consisting of an immunostimulatory ribonucleotide, a CpG oligodeoxyribonucleotide, and a combination thereof. In some embodiments, the liposome is free of CpG oligodeoxyribonucleotide.

In some embodiments, the immunostimulatory oligonucleotide is incorporated within the internal compartment of the liposome. In other embodiments, the immunostimulatory oligonucleotide is associated with the outer surface of the liposome.

In some embodiments, said immunostimulatory oligonucleotide comprises any one of SEQ ID NOs 1-14.

In certain aspects, the invention provides an adjuvant formulation comprising an immunologically effective amount of the liposomes as described herein.

In certain embodiments, the adjuvant formulation is essentially saponin-free. In certain embodiments, the adjuvant formulation is essentially free of CpG oligodeoxyribonucleotide.

In certain aspects, the invention provides a vaccine composition comprising an effective amount of an antigenic component and an immunologically effective amount of the adjuvant formulation as described herein.

In certain embodiments, the vaccine composition is essentially saponin-free.

In certain embodiments, the vaccine composition is essentially free of CpG. In certain embodiments, the antigenic component of the essentially CpG-free vaccine composition contains a (−)ssRNA virus.

In certain embodiments, the (−)ssRNA virus is an influenza virus. In some embodiments, the influenza virus is a Swine Influenza Virus.

In certain embodiments, the antigenic component is incorporated within the internal compartment of the liposome.

The antigenic component, in selected embodiments suitable for cattle, may include BVDV-1 and/or BVDV-2 inactivated viruses (and BHV-1). In other embodiments, particularly suitable for poultry animals, the antigenic component includes profilin.

DETAILED DESCRIPTION

Definitions:

The terms 'about' or 'approximately,' when used in connection with a measurable numerical variable, refer to the indicated value of the variable and to all values of the variable that are within the experimental error of the indicated value (e.g., within the 95% confidence interval for the mean) or within 10 percent of the indicated value, whichever is greater, unless 'about' is used in reference to time intervals in weeks where "about 3 weeks," is 17 to 25 days, and about 2 to about 4 weeks is 10 to 40 days.

The term 'accompanying fever' refers to rise in temperature of the vaccinated animal within one day of vaccination. In case of bovines, the term refers to rectal temperature over 103.5° F.

The term 'antigen' in combination with the species refers to pathogens causing infectious disease in said species, or to the components of these pathogens. Thus, for example, 'bovine antigens' refer to pathogens capable of causing infections disease in bovines or to the components of these pathogens.

The term 'consisting essentially of' and the like as applied to the liposomes and the adjuvant formulations of the instant invention refers to compositions which do not contain additional adjuvanting or immunomodulating agents in the amounts at which said agent exert measurable adjuvanting or immunomodulating effects.

The terms 'essentially saponin-free', 'substantially saponin-free' and the like refer to a composition that does not contain saponin in the amounts at which saponin exerts measurable adjuvanting or immunomodulating effects. In certain embodiments, essentially saponin-free compositions contain saponin in the amount insufficient to cause systemic immune response, such as fever. In certain embodiments, essentially saponin-free compositions contain no saponin or contain saponin at or below the limit of detection.

Similarly, the terms 'essentially free of CpG deoxyribonucleotide', 'substantially free of CpG deoxyribonucleotide' and the like refer to a composition which does not contain CpG deoxyribonucleotide in the amounts at which the CpG deoxyribonucleotide exerts measurable adjuvanting or immunomodulating effects. In certain embodiments, compositions essentially free of CpG deoxyribonucleotide contain no CpG deoxyribonucleotide or contain CpG deoxyribonucleotide at or below the limit of detection. The terms 'essentially free of CpG deoxyribonucleotide', 'substantially free of CpG deoxyribonucleotide' and the like specifically exclude the vaccines where the CpG deoxyribonucleotide is naturally present in the antigen.

The term 'immunostimulatory molecule' refers to a molecule that enhances an immune response.

The term 'liposome' refers to a microscopic spherical particle formed by a lipid bilayer enclosing an aqueous compartment.

The term 'parenteral administration' refers to the introduction of a substance, such as a vaccine, into a subject's body through or by way of a route that does not include the digestive tract. Parenteral administration includes subcutaneous, intramuscular, transcutaneous, intradermal, intraperitoneal, intraocular, and intravenous administration.

The terms 'therapeutically effective amount' and 'effective amount' refer to an amount of an antigen or vaccine that would induce an immune response in a subject receiving the antigen or vaccine which is adequate to prevent or reduce signs or symptoms of disease, including adverse health effects or complications thereof, caused by infection with a pathogen, such as a virus or a bacterium. Humoral immunity or cell-mediated immunity or both humoral and cell-mediated immunity may be induced. The immunogenicity and efficacy of a vaccine in an animal may be evaluated, e.g., indirectly through measurement of antibody titers, lymphocyte proliferation assays, IFN gamma ELISPOT assays, cytotoxic T cell assays or directly through monitoring signs and symptoms after challenge with wild type strain. The protective immunity conferred by a vaccine can be evaluated by measuring, e.g., reduction in clinical signs such as mortality, morbidity, fever, viremia, impact on clinical pathology, overall physical condition, and overall health and performance of the subject. The amount of a vaccine that is therapeutically effective may vary depending on the particular adjuvant used, the particular antigen used, or the condition of the subject, and can be determined by one skilled in the art.

The invention provides, in part, liposomes containing an internal compartment and an external membrane. Liposomes may have average particle size between 50 and 500 nm. In certain non-limiting embodiments, the average particle size of the liposomes of is 100-500 nm, or 150-450 nm, or 150-250 nm, or 300-400 nm, or 250-300 nm. In certain embodiments, the membrane comprises a quaternary amine compound, a phospholipid, a sterol, and a glycolipid. In certain embodiments, the liposome is essentially free of saponin.

In certain embodiments, the external membrane consists essentially or consists of the quaternary amine compound, the phospholipid, the sterol, and the glycolipid. In other embodiments, the external compartment of the liposome does not contain any immunostimulatory oligonucleotides and/or other immunomodulatory compounds. Thus, in such embodiments, the liposome consists essentially of, or consists of the internal compartment consisting essentially of or consisting of an immunologically inert aqueous vehicle, said internal compartment surrounded by the external membrane which consists essentially of, or consists of the quaternary amine compound, the phospholipid, the sterol, and the glycolipid.

Quaternary amine compounds are ammonium based compounds with four hydrocarbon groups. In practice, hydrocarbon groups are generally limited to alkyl or aryl groups. In a set of embodiments, the quaternary amine compounds are composed of four alkyl chains, two of which are C10-C20 alkyls and the remaining two are C1-C4 alkyls. In certain embodiments, the quaternary amine is dimethyldioctadecylammonium (DDA) bromide, chloride or another pharmaceutically acceptable counter ion.

Sterols share a common chemical core, which is a steroid ring structure[s], having a hydroxyl (OH) group, usually attached to carbon-3. The hydrocarbon chain of the fatty-acid substituent varies in length, usually from 16 to 20 carbon atoms, and can be saturated or unsaturated. Sterols commonly contain one or more double bonds in the ring structure and also a variety of substituents attached to the rings. Sterols and their fatty-acid esters are essentially water-insoluble. In view of these chemical similarities, it is thus likely that the sterols sharing this chemical core would have similar properties when used in the vaccine compositions of the instant invention. Sterols are well known in the art and can be purchased commercially. For example cholesterol is disclosed in the Merck Index, 12th Ed., p. 369. Suitable sterols include, without limitations, β-sitosterol, stigmasterol, ergosterol, ergocalciferol, and cholesterol.

Suitable glycolipids are generally those which activate the Th2 response. The glycolipids include, without limitations, those encompassed by Formula I and that are generally described in US Patent Publication 20070196384 (Ramasamy et al).

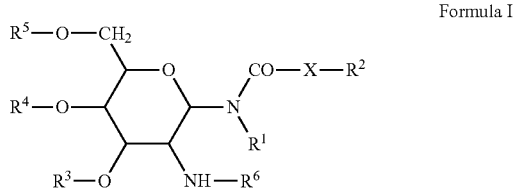

Formula I

In the structure of Formula I, $R^1$ and $R^2$ are independently hydrogen, or a saturated alkyl radical having up to 20 carbon atoms; X is —$CH_2$—, —O— or —NH—; $R^2$ is hydrogen, or a saturated or unsaturated alkyl radical having up to 20 carbon atoms; $R^3$, $R^4$, and $R^5$ are independently hydrogen, —$SO_4^{2-}$, —$PO_4^{2-}$, —$COC_{1-10}$ alkyl; $R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenylalany, L-prolyl, L-seryl, L-threonyl, L-tyrosyl, L-tryptophanyl, and L-valyl or their D-isomers.

Examples of a glycolipid are, without limitation, N-(2-Deoxy-2-L-leucylamino-β-D-glucopyranosyl)-N-octadecyldodecanoylamide (BayR® 1005, or R1005) or a salt (e.g., an acetate) thereof.

Lecithin can be obtained as a mixture of phosphatides and triglycerides by water-washing crude vegetable oils, and separating and drying the resulting hydrated gums. A refined product can be obtained by fractionating the mixture for acetone insoluble phospholipids and glycolipids remaining after removal of the triglycerides and vegetable oil by acetone washing. Alternatively, lecithin can be obtained from various commercial sources.

Other suitable phospholipids include phosphatidylcholine, phosphatidylglycerol, phosphatidylinositol, phosphatidylserine, acylphosphatidylethanolamine, diphosphatidlglcerol, lysophosphatidylethanolamine, lysophosphatidylcholine, phosphatidic acid, cardiolipin, and phosphatidylethanolamine. The phospholipids may be isolated from natural sources or conventionally synthesized.

The liposomes as described herein allow for flexible ratios of the elements of the external membrane. In certain embodiments, the weight ratios of the quaternary ammonium compound: the sterol: the phospholipid: the glycolipid are 1:0.75-1.25:1.5-2.5:1.5-2.5, respectively. In certain embodiments, the weight ratios of the quaternary ammonium compound: the sterol: the phospholipid: the glycolipid are 1:1:2:2.

In other embodiments, the total weight of the quaternary ammonium compound and the sterol is about the half (e.g., 40%, 45%, 50%, 55%, 60%) of the total weight of the glycolipid and the phospholipid, provided that the quaternary ammonium compound comprises at least about 5% w/w of the total weight of these four compounds (the quaternary ammonium compound, the sterol, the phospholipid, and the glycolipid), and the glycolipid is at least about 20% w/w of the total weight of these four compounds.

In certain embodiments, the total weight of the quaternary ammonium compound and the sterol is about 10-40% (e.g., about 10%, about 15%, about 20%, about 25%, about 30%, about 33.3%, about 35%, about 40%) of the total weight of the glycolipid and the phospholipid, provided that the quaternary ammonium compound comprises at least about 5% w/w of the total weight of these four compounds (the quaternary ammonium compound, the sterol, the phospholipid, and the glycolipid), and the glycolipid is at least about 20% w/w of the total weight of these four compounds.

The liposomes of the instant invention may be administered as an adjuvant, e.g., in immunologically effective amounts, thus forming a vaccine combination comprising the adjuvant composition containing the liposomes, and the antigenic component, as further described below.

The weight of the client species ultimately dictates the dose of the adjuvant composition of the instant invention.

In certain embodiments, suitable for cattle, horses, and adult pigs, one dose contains the equivalent of 1000-3000 μg of external membrane component (i.e., the total weight of the quaternary ammonium compound, the sterol, the phospholipid, and the glycolipid), or the equivalent of 1000-2000 μg, or the equivalent of 1000-1500 μg, or the equivalent of 1300-1800 μg, or the equivalent of 1500-2000 μg.

The weight of the liposome composition may not be equal to the weight of the membrane component due to the presence of the internal compartment which may contain the immunostimulatory oligonucleotide, the antigen component, other immunomodulators, etc. The use of equivalents to the liposomal membrane component allows for the uniform dosing. The dosing regimen recited therein ensures that the cattle animal receives at least 200 μg of the glycolipid and about 50 μg of the quaternary ammonium compound.

In certain embodiments suitable for sheep and goats, one dose contains the equivalent of 300-1000 μg of external membrane component, e.g., the equivalents of 300-500 μg, or the equivalents of 400-500 μg, or the equivalents of 400-1000 μg, or the equivalents of 500-1000 μg, or the equivalents of 600-1000 μg, or the equivalents of 600-800 μg.

In certain embodiments suitable for piglets, dogs, and cats, one dose contains the equivalent of 100-400 μg of external membrane component, or the equivalent of 100-200 μg, or the equivalent of 100-150 μg, or the equivalent of 130-180 μg, or the equivalent of 150-200 μg.

In certain embodiments suitable for poultry, one dose contains the equivalent of 50-200 μg of external membrane component, or the equivalent of 50-100 μg, or the equivalent of 50-75 μg, or the equivalent of 65-90 μg, or the equivalent of 75-100 μg, or the equivalent of 75-150 μg.

The internal compound of the liposome may contain antigens or other immunomodulatory molecules. In certain embodiments, such immunomodulatory molecules suitable for the internal compartment include, without limitation, antigen extracts, subunits, synthetics, whole cell or virus.

In certain embodiments, active pharmaceuticals may be packaged inside a liposome.

Immunomodulators that could be packaged also include, without limitations, rmLT, MPLA, Alpha-Gal-Cer. Cholera toxin, LPS, lipoteichoic acids, poly I:C, flagellin, zymosan, chitin and modified chitin forms, beta-glucans, avridine, inulin and modified inulin forms, ethylene malic anhydries, pluronics like L121 and L141, CD40 agonist, TLR5 agonist as well as any TLR agonist, GM-CSF.

In certain embodiments, liposomes may carry various molecules that could be used as markers, including without limitations, OspA, OspC, pertactin and others.

In certain embodiments, the adjuvant composition of the instant invention further comprises immunostimulatory oligonucleotides, such as, for example, CpG oligodeoxyribonucleotides or immunostimulatory oligoribonucleotides (ORNs), or chimeras thereof. Suitable non-limiting examples of CpG oligodeoxyribonucleotides are illustrated in SEQ ID NOs 1-10, suitable non-limiting examples of ORNs are provided in SEQ ID NOs 11-13, and a suitable non-limiting example of a chimeric immunostimulatory oligonucleotide is provided in SEQ ID NO: 14.

These immunostimulatory oligonucleotides are, in some embodiments, present in the internal compartment of the liposome.

In certain embodiments, the immunomodulatory oligonucleotides are associated with the outer surface of the liposome. The association may be due to hydrogen bonds, electrostatic bonds, lipophilic bonds, Van der Waals forces, and the like.

In certain embodiments, the negatively charged immunostimulatory oligonucleotide is associated with the outer surface of the liposome due to interaction with the positively charged quaternary nitrogen atom in the quaternary ammonium compound.

CpG oligodeoxyribonucleotides (also referred to as CpG deoxyribonucleotides or CpG ODN) are a recently described class of pharmacotherapeutic agents that are characterized by the presence of an unmethylated CG dinucleotide in specific base-sequence contexts (CpG motif). (Hansel T T, Barnes P J (eds): New Drugs for Asthma, Allergy and COPD. Prog Respir Res. Basel, Karger, 2001, vol 31, pp 229-232, which is incorporated herein by reference). These CpG motifs are not seen in eukaryotic DNA, in which CG dinucleotides are suppressed and, when present, usually methylated, but are present in bacterial DNA to which they confer immunostimulatory properties.

In certain embodiments, the adjuvants of the instant invention utilize a so-called P-class immunostimulatory oligonucleotide, more preferably, modified P-class immunostimulatory oligonucleotides, even more preferably, E-modified P-class oligonucleotides. P-class immunostimulatory oligonucleotides are CpG oligodeoxyribonucleotide characterized by the presence of palindromes, generally 6-20 nucleotides long. The P-Class oligonucleotides have the ability to spontaneously self-assemble into concatamers either in vitro and/or in vivo. These oligonucleotides are, in a strict sense, single-stranded, but the presence of palindromes allows for formation of concatamers or possibly stem-and-loop structures. The overall length of P-class immunostimulatory oligonucleotides is between 19 and 100 nucleotides, e.g., 19-30 nucleotides, 30-40 nucleotides, 40-50 nucleotides, 50-60 nucleotides, 60-70 nucleotides, 70-80 nucleotides, 80-90 nucleotides, 90-100 nucleotides.

In one aspect of the invention the immunostimulatory oligonucleotide contains a 5' TLR activation domain and at least two palindromic regions, one palindromic region being a 5' palindromic region of at least 6 nucleotides in length and connected to a 3' palindromic region of at least 8 nucleotides in length either directly or through a spacer.

The P-class immunostimulatory oligonucleotides may be modified according to techniques known in the art. For example, J-modification refers to iodo-modified nucleotides. E-modification refers to ethyl-modified nucleotide(s). Thus, E-modified P-class immunostimulatory oligonucleotides are P-class immunostimulatory oligonucleotides, wherein at least one nucleotide (preferably 5' nucleotide) is ethylated. Additional modifications include attachment of 6-nitro-benzimidazol, O-Methylation, modification with proynyl-dU, inosine modification, 2-bromovinyl attachment (preferably to uridine).

The P-class immunostimulatory oligonucleotides may also contain a modified internucleotide linkage including, without limitations, phosphodiester linkages and phosphorothioate linkages. The oligonucleotides of the instant invention may be synthesized or obtained from commercial sources.

P-Class oligonucleotides and modified P-class oligonucleotides are further disclosed in published PCT application no. WO2008/068638, published on Jun. 12, 2008. Suitable non-limiting examples of modified P-class immunostimulatory oligonucleotides are provided below (In SEQ ID NOs 1-10, "*" refers to a phosphorothioate bond and "_" refers to a phosphodiester bond). In SEQ ID NOs 11-14, all bonds are either phosphodiester or phosphorothioate bonds.

```
                                         SEQ. ID NO: 1
5' T*C_G*T*C_G*A*C_G*A*T*C_G*G*C*G*C_G*C*G*C*C*G
3'
                                         SEQ. ID NO: 2
5' T*C_G*A*C*G*T*C*G*A*T*C*G*G*C*G*C*G*C*G*C*C*G
3'
                                         SEQ. ID NO: 3
5' T*C*G*A*C*G*T*C*G*A*T*C*G*G*C*G*C*G*C*G*C*C*G*T
3'
                                         SEQ. ID NO: 4
5' JU*C_G*A*C*G*T*C*G*A*T*C*G*G*C*G*C*G*C*G*C*C*G
3'
                                         SEQ. ID NO: 5
5' JU*C_G*A*C*G*T*C*G*A*T*C*G*G*C*G*C*G*C*G*C*C*
G*T 3'
                                         SEQ. ID NO: 6
5' JU*C*G*A*C*G*T*C*G*A*T*C*G*G*C*G*C*G*C*G*C*C*
G*T 3'
                                         SEQ. ID NO: 7
5' EU*C_G*A*C*G*T*C*G*A*T*C*G*G*C*G*C*G*C*G*C*C*G
3'
                                         SEQ. ID NO: 8
5' JU*C_G*T*C*G*A*C*G*A*T*C*G*G*C*G*G*C*C*G*C*C*
G*T 3'
                                         SEQ. ID NO: 9
5' JU*C*G*T*C*G*A*C*G*A*T*C*G*G*C*G*G*C*C*G*C*C*
G*T 3'
                                         SEQ. ID NO: 10
5' T*C_G*T*C_G*A*C_G*A*T*C_G*G*C*G*C_G*C*G*C*C*G
3'
                                         SEQ. ID NO: 11
5'-UUGUUGUUGUUGUUGUUGUU-3'
                                         SEQ. ID NO: 12
5'-UUAUUAUUAUUAUUAUUAUU-3'
                                         SEQ. ID NO: 13
5'-AAACGCUCAGCCAAAGCAG-3'
                                         SEQ. ID NO: 14
5'-dTdCdGdTdCdGdTdTdTrGrUrUrGrUdTdTdT-3'
```

The dose of the immunostimulatory oligonucleotide for use in the adjuvant compositions ultimately depends upon the intended species.

For example, in certain embodiments suitable for cattle, sheep or adult swine, one dose of the adjuvant composition of the instant invention would comprise between about 50 and 400 µg (e.g., 50-300, or 100-250 µg, or about 50 to about 100 µg for adult pigs and about 100 to about 250 µg for cattle) of the immunostimulatory oligonucleotide.

In certain embodiments suitable for companion animals or piglets, one dose of the adjuvant composition of the instant invention would comprise between about 5 and 100 µg (e.g., 10-80 µg, or 20-50 µg) of the immunostimulatory oligonucleotide.

In certain embodiments suitable for poultry, one dose of the adjuvant composition of the instant invention would between about 0.1 and about 5 µg (e.g., 0.5-3 µg, or 0.9-1.1 µg) of immunostimulatory oligonucleotide.

Methods of making liposomes are well known in the art. Briefly, the components of the liposome are dissolved and mixed in an organic solvent, e.g., methylene chloride, and then the solvent is removed by drying to yield a film. The film is later rehydrated using an aqueous media (e.g., water or a buffer) which optionally contains compounds which are to be incorporated within the internal compartment of the liposomes. In different embodiments, the compounds may include the immunostimulatory oligonucleotides, other immunomodulators, and/or the antigen component.

The step of rehydration is followed by sonication and/or extrusion to reduce the size of the vesicles formed during the rehydration step.

There are two main sonication techniques: probe/tip sonication and bath sonication. Probe/tip sonication has a high energy input which causes significant heat generation, therefore necessitating the use of an ice bath to maintain temperature of the liposomal dispersion in order to prevent lipid degradation. Alternatively, ultrasonic energy can be indirectly imparted to the liposome suspension using a bath sonicator, where temperature is easier to control but energy loss is comparatively high. Sonication generally yields small vesicles (~10 nm) which spontaneously fuse over time to relieve the stress of high membrane curvature.

The extrusion method involves passing the liposome suspension through a membrane with defined pore size. This method is advantageous because the defined pore size encourages homogeneity of particle size within the liposome population, though extrusion below lipid transition temperature can be difficult owing to membrane rigidity. Liposome suspensions are often extruded multiple times to achieve low polydispersity in the final product.

It may be desirable to prepare storage-stable preparation of liposomes. In certain embodiments, such storage-stable preparation of liposomes is created by freeze-drying. Briefly, the dry film described above, is rehydrated in an aqueous buffer containing a cryoprotectant and lyoprotectant such as sucrose, trehalose, or a combination thereof. In other embodiments, the cryoprotectant and lyoprotectant are added after the rehydration step. The rehydrated preparation is then lyophilized using techniques well known in the art. The resulting lyophilized preparation is storage-stable. At the desired time, it can be rehydrated with suitable buffer.

Additional immunomodulators, including, without limitations, the immunostimulatory oligonucleotides and the antigen(s) may be added either before the freeze-drying or at the time of final preparation.

In certain embodiments, the antigens are admixed with the liposomal formulation after the liposomes of the instant invention are reconstituted. In other embodiments, the liposomes, the additional immunomodulators, and the antigenic component are prepared and dried together.

In certain embodiments, additional immunostimulatory compounds are present in the compositions of the instant invention. Such additional immunostimulatory compounds may be present within the internal compartment of the liposomes, and/or associated with the outer surface of the liposomes, and/or independently of the liposomes, in the adjuvant compositions of the instant invention.

Suitable non-limiting examples of such additional immunostimulatory compounds include, but not limited to several adjuvant classes such as mineral salts, e.g., Alum, aluminum hydroxide, aluminum phosphate and calcium phosphate; surface-active agents and microparticles, e.g., nonionic block polymer surfactants, virosomes, saponins (e.g., Quil A, QS-21 and GPI-0100), proteosomes, immune stimulating complexes, cochleates, pyridine, vitamin A, vitamin E; bacterial products such as the RIBI adjuvant system (Ribi Inc.), cell wall skeleton of *Mycobacterium phlei* (Detox®), muramyl dipeptides (MDP) and tripeptides (MTP), monophosphoryl lipid A (MPLA), *Bacillus* Calmete-Guerin (BCG), heat labile *E. coli* enterotoxins, cholera toxin, trehalose dimycolate, cytokines and hormones, e.g., interleukins (IL-1, IL-2, IL-6, IL-12, IL-15, IL-18), granulocyte-macrophage colony stimulating factor, dehydroepiandrosterone, 1,25-dihydroxy vitamin $D_3$; polyanions, e.g., dextran; polyacrylics (e.g., polymethylmethacrylate, CARBOPOL®934P); carriers e.g., tetanus toxoid, diptheria toxoid, cholera toxin B subunit, mutant heat labile enterotoxin of enterotoxigenic *E. coli* (rmLT), heat shock proteins; oil-in-water emulsions e.g., AMPHIGEN® (Hydronics, USA); polycationic carriers (e.g., DEAE Dextran or QAE Dextran), and water-in-oil emulsions such as, e.g., Freund's complete and incomplete adjuvants.

Other suitable immunomodulators include Alpha-Gal-Cer. LPS, lipoteichoic acids, poly I:C, flagellin, zymosan, chitin and modified chitin forms, beta-glucans, avridine, inulin and modified inulin forms, ethylene malic anhydries, pluronics like L121 and L141, CD40 agonist, TLR5 agonist as well as any TLR agonist.

Antigens and Diseases

In certain embodiments, the liposomal adjuvant composition of the instant invention may be combined with an antigenic component thus forming the vaccine composition of the instant invention. The antigenic component of the vaccines of the instant invention may be present within the internal compartment of the liposomes, and/or associated with the outer surface of the liposomes, and/or independently of the liposomes.

In certain embodiments, the vaccine composition is substantially saponin-free. In additional embodiments, the vaccine composition is essentially free of CpG deoxyribonucleotide.

The embodiments wherein the vaccine composition is essentially free of CpG deoxyribonucleotide are preferred if the antigen in the vaccine contains a whole ssRNA virus (either a (+)ssRNA or a (−)ssRNA virus) sequences that are immunostimulatory though targeting TLR7/8. Such TLR 7/8 stimulatory sequences include polyU or GU-rich ssRNA sequences. Heil F, Hemmi H. et al., 2004. *Science* 303 (5663):1526-9. Diebold S S., Kaisho T. et al., 2004. *Science* 303(5663):1529-31.

The viruses containing such sequences include, without limitations, different influenza viruses (e.g., bovine influenza virus, canine influenza virus, equine influenza virus, swine influenza virus and the like). In particularly preferred embodiments, the antigenic component of vaccine essentially free of CpG ODN contains influenza virus.

An antigenic component may include, in different exemplary embodiments, bovine antigens, caprine antigens, porcine antigens, poultry antigens, equine antigens, canine antigens, equine antigens and feline antigens.

Antigens can be any of a wide variety of substances capable of producing a desired immune response in a subject, including, without limitations, one or more of viruses (inactivated, attenuated, and modified live), bacteria, parasites, nucleotides (including, without limitation nucleic-acid based antigens, e.g., DNA vaccines or mRNA vaccines), polynucleotides, peptides, polypeptides, recombinant proteins, synthetic peptides, protein extract, cells (including tumor cells), tissues, polysaccharides, carbohydrates, fatty acids, lipoteichioc acid, peptidoglycans, lipids, or glycolipids, individually or in any combination thereof.

Antigens used with the adjuvants of the invention also include immunogenic fragments of nucleotides, polynucleotides, peptides, polypeptides, that can be isolated from the organisms referred to herein, or chemically or biologically manufactured.

Live, modified-live, and attenuated viral strains that do not cause disease in a subject have been isolated in non-virulent form or have been attenuated using methods well known in the art, including serial passage in a suitable cell line or exposure to ultraviolet light or a chemical mutagen. Inactivated or killed viral strains are those which have been inactivated by methods known to those skilled in the art, including treatment with formalin, beta-propriolactone (BPL), peroxides, binary ethyleneimine (BEI), sterilizing radiation, heat, or other such methods.

Two or more antigens can be combined to produce a polyvalent composition that can protect a subject against a wide variety of diseases caused by the pathogens. Currently, commercial manufacturers of vaccines, as well as end users, prefer polyvalent vaccine products. While conventional adjuvants are often limited in the variety of antigens with which they can be effectively used (either monovalently or polyvalently), the adjuvants described herein can be used effectively with a wide range of antigens, both monovalently and polyvalently. Thus, the antigens described herein can be combined in a single composition comprising the adjuvants described herein.

Examples of bacteria which can be used as antigens with the adjuvant compositions described herein include, but are not limited to, *Acinetobacter calcoaceticus, Acetobacter paseruianus, Actinobacillus pleuropneumoniae, Aeromonas hydrophila, Alicyclobacillus acidocaldarius, Arhaeglobus fulgidus, Bacillus pumilus, Bacillus stearothermophillus, Bacillus subtilis, Bacillus thermocatenulatus, Bordetella bronchiseptica, Burkholderia cepacia, Burkholderia glumae, Campylobacter coli, Campylobacter fetus, Campylobacter jejuni, Campylobacter hyointestinalis, Chlamydia psittaci, Chlamydia trachomatis, Chlamydophila* spp., *Chromobacterium viscosum, Erysipelothrix rhusiopathieae, Listeria monocytogenes, Ehrlichia canis, Escherichia coli, Haemophilus influenzae, Haemophilus somnus, Helicobacter suis, Lawsonia intracellularis, Legionella pneumophilia, Moraxellsa* sp., *Mycobactrium bovis, Mycoplasma hyopneumoniae, Mycoplasma mycoides* subsp. *mycoides* LC, *Clostridium perfringens, Odoribacter denticanis, Pasteurella* (*Mannheimia*) *haemolytica, Pasteurella multocida, Photorhabdus luminescens, Porphyromonas gulae, Porphyromonas gingivalis, Porphyromonas salivosa, Propionibacterium acnes, Proteus vulgaris, Pseudomonas wisconsinensis, Pseudomonas aeruginosa, Pseudomonas fluorescens* C9, *Pseudomonas fluorescens* SIKW1, *Pseudomonas fragi, Pseudomonas luteola, Pseudomonas oleovorans, Pseudomonas* sp B11-1, *Alcaliges eutrophus, Psychrobacter immobilis, Rickettsia prowazekii, Rickettsia rickettsii, Salmonella enterica* all serovars, including for example: *Salmonella enterica Typhimurium, Salmonella enterica Bongori, Salmonella enterica* Dublin, *Salmonella enterica Choleraesuis*, and *Salmonella enterica* Newport, *Serratia marcescens, Spirluina platensis, Staphylococcus aureus, Staphylococcus epidermidis, Staphylococcus hyicus, Streptomyces albus, Streptomyces cinnamoneus, Streptococcus uberis, Streptococcus suis, Streptomyces exfoliates, Streptomyces scabies, Sulfolobus acidocaldarius, Syechocystis* sp., *Vibrio cholerae, Borrelia burgdorferi, Treponema denticola, Treponema minutum, Treponema phagedenic, Treponema refringens, Treponema vincentii, Treponema palladium, Trueperella pyogenes* and *Leptospira* species, such as the known pathogens *Leptospira canicola, Leptospira grippotyposa, Leptospira hardjo, Leptospira borgpetersenii hardjo-bovis, Leptospira borgpetersenii hardjo-prajitno, Leptospira interrogans, Leptospira icterohaemorrhagiae, Leptospira pomona*, and *Leptospira bratislava*, and combinations thereof.

Both inactivated viruses and attenuated live viruses may be used in the adjuvant compositions. Some examples of viruses which can be used as antigens include, but are not limited to, Avian herpesviruses, Bovine herpesviruses, Canine herpesviruses, Equine herpesviruses, Feline viral rhinotracheitis virus, Marek's disease virus, Ovine herpesviruses, Porcine herpesviruses, Porcine Epidemic Diarrhea virus (PEDv), Pseudorabies virus, Avian paramyxoviruses, Bovine respiratory syncytial virus, Canine distemper virus, Canine parainfluenza virus, canine adenovirus, canine parvovirus, Bovine Parainfluenza virus 3, Ovine parainfluenza 3, Rinderpest virus, Border disease virus, Bovine viral diarrhea virus (BVDV), BVDV Type I, BVDV Type II, Classical swine fever virus, Avian Leukosis virus, Bovine immunodeficiency virus, Bovine leukemia virus, Bovine tuberculosis, Equine infectious anemia virus, Feline immunodeficiency virus, Feline leukemia virus (FeLV), Newcastle Disease virus, Ovine progressive pneumonia virus, Ovine pulmonary adenocarcinoma virus, Canine coronavirus (CCV), pantropic CCV, Canine respiratory coronavirus, Bovine coronavirus, Feline Calicivirus, Feline enteric coronavirus, Feline infectious peritonitis, virus, Porcine epidemic diarrhea virus, Porcine hemagglutinating encephalomyletitis virus, Porcine parvovirus, Porcine Circovirus (PCV) Type I, PCV Type II, Porcine Reproductive and Respiratory Syndrome (PRRS) Virus, Transmissible gastroenteritis virus, Turkey coronavirus, Bovine ephemeral fever virus, Rabies, Rotovirus, Vesicular stomatitis virus, lentivirus, Avian influenza, Rhinoviruses, Equine influenza virus, Swine influenza virus, Canine influenza virus, Feline influenza virus, Human influenza virus, Eastern Equine encephalitis virus (EEE), Venezuelan equine encephalitis virus, West Nile virus, Western equine encephalitis virus, human immunodeficiency virus, human papilloma virus, varicella zoster virus, hepatitis B virus, rhinovirus, and measles virus, and combinations thereof.

Examples of peptide antigens include *Bordetella bronchiseptica* p68, GnRH, IgE peptides, Fel d1, and cancer antigens, and combinations thereof. Examples of other antigens include nucleotides, carbohydrates, lipids, glycolipids, peptides, fatty acids, lipoteichoic and teichoic acid, and peptidoglycans, and combinations thereof.

Examples of parasites which can be used as antigens with the adjuvant compositions described herein include, but are not limited to, *Anaplasma, Fasciola hepatica* (liver fluke), *Coccidia, Eimeria* spp., *Neospora caninum, Toxoplasma gondii, Giardia, Dirofilaria* (heartworms), *Ancylostoma* (hookworms), *Cooperia, Haemonchus contortus* (Barber pole worm), *Ostertagia ostertagi* (stomach worm), *Dictyocaulus viviparous* (lung worms), *Trypanosoma* spp., *Leishmania* spp., *Trichomonas* spp., *Cryptosporidium parvum, Babesia, Schistosoma, Taenia, Strongyloides, Ascaris, Trichinella, Sarcocystis, Hammondia,* and *Isopsora,* and combinations thereof. Also contemplated are external parasites including, but not limited to, ticks, including *Ixodes, Rhipicephalus, Dermacentor, Amblyomma, Boophilus, Hyalomma,* and *Haemaphysalis* species, and combinations thereof.

The amount of antigen used to induce an immune response will vary considerably depending on the antigen used, the subject, and the level of response desired, and can be determined by one skilled in the art. For vaccines containing modified live viruses or attenuated viruses, a therapeutically effective amount of the antigen generally ranges from about $10^2$ Tissue Culture Infective Dose $(TCID)_{50}$ to about $10^{10}$ $TCID_{50}$, inclusive. For many such viruses, a therapeutically effective dose is generally in the range of about $10^2$ $TCID_{50}$ to about $10^8$ $TCID_{50}$, inclusive. In some embodiments, the ranges of therapeutically effective doses are about $10^3$ $TCID_{50}$ to about $10^6$ $TCID_{50}$, inclusive. In some other embodiments, the ranges of therapeutically effective doses are about $10^4$ $TCID_{50}$ to about $10^5$ $TCID_{50}$, inclusive.

For vaccines containing inactivated viruses, a therapeutically effective amount of the antigen is generally at least about 100 relative units per dose, and often in the range from about 1,000 to about 4,500 relative units per dose, inclusive. In other embodiments, the therapeutically effective amount of the antigen is in a range from about 250 to about 4,000 relative units per dose, inclusive, from about 500 to about 3,000 relative units per dose, inclusive, from about 750 to about 2,000 relative units per dose, inclusive, or from about 1,000 to about 1,500 relative units per dose, inclusive.

A therapeutically effective amount of antigen in vaccines containing inactivated viruses can also be measured in terms of Relative Potency (RP) per mL. A therapeutically effective amount is often in the range from about 0.1 to about 50 RP per mL, inclusive. In other embodiments, the therapeutically effective amount of the antigen is in a range from about 0.5 to about 30 RP per mL, inclusive, from about 1 to about 25 RP per mL, inclusive, from about 2 to about 20 RP per mL, inclusive, from about 3 to about 15 RP per mL, inclusive, or from about 5 to about 10 RP per mL, inclusive.

The number of cells for a bacterial antigen administered in a vaccine ranges from about $1\times10^6$ to about $5\times10^{10}$ colony forming units (CFU) per dose, inclusive. In other embodiments, the number of cells ranges from about $1\times10^7$ to $5\times10^{10}$ CFU/dose, inclusive, or from about $1\times10^8$ to $5\times10^{10}$ CFU/dose, inclusive. In still other embodiments, the number of cells ranges from about $1\times10^2$ to $5\times10^{10}$ CFU/dose, inclusive, or from about $1\times10^4$ to $5\times10^9$ CFU/dose, inclusive, or from about $1\times10^5$ to $5\times10^9$ CFU/dose, inclusive, or from about $1\times10^6$ to $5\times10^9$ CFU/dose, inclusive, or from about $1\times10^6$ to $5\times10^8$ CFU/dose, inclusive, or from about $1\times10^7$ to $5\times10^9$ CFU/dose, inclusive.

The number of cells for a parasite antigen administered in a vaccine ranges from about $1\times10^2$ to about $1\times10^{10}$ per dose, inclusive. In other embodiments, the number of cells ranges from about $1\times10^3$ to about $1\times10^9$ per dose, inclusive, or from about $1\times10^4$ to about $1\times10^8$ per dose, inclusive, or from about $1\times10^5$ to about $1\times10^7$ per dose, inclusive, or from about $1\times10^6$ to about $1\times10^8$ per dose, inclusive.

Excipients

Adjuvant formulation and/or vaccine compositions may include a pharmaceutically acceptable carrier. As used herein, "a pharmaceutically-acceptable carrier" includes any and all solvents, dispersion media, coatings, stabilizing agents, diluents, preservatives, antibacterial and antifungal agents, isotonic agents, adsorption delaying agents, and the like. The carrier(s) must be "acceptable" in the sense of being compatible with the other components of the compositions and not deleterious to the subject. Typically, the carriers will be sterile and pyrogen-free, and selected based on the mode of administration to be used. It is well known by those skilled in the art that the preferred formulations for the pharmaceutically acceptable carrier which comprise the compositions are those pharmaceutical carriers approved in the applicable regulations promulgated by the United States (US) Department of Agriculture or US Food and Drug Administration, or equivalent government agency in a non-US country. Therefore, the pharmaceutically accepted carrier for commercial production of the compositions is a carrier that is already approved or will be approved by the appropriate government agency in the US or foreign country.

Administration of the Compositions

Dose sizes of compositions typically range from about 1 mL to about 5 mL, inclusive, depending on the subject and the antigen. For example, for a canine or feline, a dose of about 1 mL is typically used, while in cattle a dose of about 2-5 mL is typically used. However, these adjuvants also can be formulated in microdoses, wherein doses of about 100 µL can be used.

The routes of administration for adjuvant compositions include parenteral, oral, oronasal, intranasal, intratracheal, subcutaneous, intramuscular, transcutaneous, intradermal, intraperitoneal, intraocular, intravenous administration and in ova. Any suitable device may be used to administer the compositions, including syringes, droppers, needleless injection devices, patches, and the like. The route and device selected for use will depend on the composition of the adjuvant, the antigen, and the subject and such are well known to the skilled artisan.

Use of the Compositions

The adjuvant formulations described herein are easy to manufacture and stable for at least 18 months at 4° C. Formulations may be stable, for example, for about 18 months, or about 18 to about 24 months at 4° C. In another embodiment the formulations are stable for at least about 24 months at 4° C. Accelerated testing procedures also indicate that the formulations described herein are stable for at least two weeks at 37° C. which corresponds to about 24 months at 4° C.

The adjuvant compositions described herein can be safely and effectively administered to a wide range of subjects. It has been surprisingly found that the adjuvant compositions described herein demonstrate safety improvements when compared with other adjuvant compositions.

The following examples are presented as illustrative embodiments, but should not be taken as limiting the scope of the invention. Many changes, variations, modifications, and other uses and applications of this invention will be apparent to those skilled in the art.

EXAMPLES

Example 1—Characterization of Liposomes

DCRL liposomes (containing DDA, Cholesterol, Bay®R1005, and Lecithin) were adjusted to a final concentration of 50, 50, 100 and 100 µg/mL of DDA, cholesterol, R1005 and soy lecithin, respectively.

The compounds were added to a 250 mL round bottom flask and filled to a final volume of 5 mL with anhydrous grade chloroform (Sigma-Aldrich, Poole, Dorset, UK) using 1 mL Solvent Safe™ pipettor tips (Sigma-Aldrich). Solvent was removed using a rotary evaporator (Büchi, Flawil, Switzerland) at 55° C. under vacuum (KNF Neuberger, Witney, Oxfordshire, UK) for 1 hour until a dry, white lipid film formed. Liposomes were rehydrated with either double distilled water (ddH$_2$O) from an in-house modified Option 3 water purifier including reverse osmosis for ultra-high purity (ELGA LabWater, Wycombe, Buckinghamshire, UK) or phosphate-buffered saline (PBS; Sigma-Aldrich) reconstituted from tablets with ddH$_2$O.

After rehydration, liposomes were handled with 1 mL wide orifice pipettor tips (VWR, Lutterworth, Leicestershire, UK) to reduce shearing. Then, the liposome suspension was sonicated in a bath (Sarose Scientific Instruments, Perivale, Middlesex, UK) for 1 hour and/or extruded up to 3 times through a 100 nm polycarbonate Whatman® Nucleopore Track-Etched Membrane (Sigma-Aldrich) using a mini extruder cell fitted with two 1 mL syringes. Polycarbonate membrane was flanked by 10 mm filter supports.

Sonicated DCRL liposomes (1.14 µm average diameter) were significantly larger (5.44-fold) than extruded liposomes. Sonication followed by extrusion did not significantly affect vesicle size compared to extruded samples (209.6 nm). Polydispersity of extruded liposomes was 2.10-fold lower than sonicated liposomes. A combination of sonication and extrusion significantly increased DCRL polydispersity 1.42-fold compared to extruded liposomes.

To evaluate the colloidal stability of liposomes in aqueous solution, DCRL liposomes hydrated in ddH$_2$O were assessed over 4 weeks. Notably, an approximate thermodynamic equivalent of 2 years at 4° C. is storage for 4 weeks at 37° C., thus motivating assessment of product stability at both 4 and 37° C. Both empty ("−ODN") DCRL liposomes and DCRL liposomes loaded with an exemplary immunostimulatory oligonucleotide CpG ODN ("+ODN") were assessed to determine the effect of anionic nucleic acids on cationic liposomal colloidal stability. Here, ODN was loaded by rehydrating lipid film with a solution of ddH$_2$O and ODN. Size and polydispersity of DCRL liposomes hydrated in ddH$_2$O (177 nm, 0.24) were statistically similar to those hydrated in PBS (210 nm, 0.17).

At 4° C., +/−ODN DCRL liposomes underwent insignificant 1.10- and 1.01-fold increases in diameter after 28 days, respectively. Liposomes containing ODN (+ODN liposomes) (417 nm) were significantly larger than liposomes lacking ODN (−ODN liposomes) (177 nm). Similarly, polydispersity decreased modestly 1.08- and 1.03-fold for +/−ODN liposomes after 28 days, respectively, though polydispersity at day 28 was significantly higher in +ODN liposomes (1.23-fold) compared to −ODN counterparts.

Conversely, aggregation behavior of the liposomes was observed after 28 days when stored at 37° C. +/−ODN liposomes underwent significant 3.24- and 2.00-fold increases in diameter after 28 days, respectively, but stabilized after day 21. While +ODN liposomes were larger (1.46-fold at day 28) than −ODN liposomes owing to ODN-mediated charge compensation and loss of colloidal stability, stability trends over time were qualitatively similar. However, destabilization of +ODN liposomes occurred after day 7, whereas in −ODN liposomes, stability was maintained until after day 14. Additionally, polydispersity of +/−ODN liposomes were statistically similar after 28 days, having undergone significant 1.92- and 1.50-fold reductions, respectively, in polydispersity compared to vesicles at day 0.

These results suggest the need for development of technologies for preservation of the liposome and also suggest that more powerful sonication and/or extrusion techniques resulting in an initially smaller liposome size may compensate for initial aggregation of liposomes.

Sizes of liposomes prepared using microfluidization (Microfluidics Corp., Model 110EH) and sonication were compared. When the step of sonication was replaced with microfluidization, the formulation yielded liposomes having mean diameter of about 59 nm.

These results demonstrate that liposomes prepared using microfluidization can minimize the aggregation of the liposomes which may potentially be caused by the addition of ODN or ORN.

Example 2—Stability of Lyophilized Liposomes

Lyophilization was performed using a Dura-Stop freeze-dryer (SP Scientific, Ipswich, Suffolk, UK). Samples were filled into 10 mL tubular type I glass freeze-drying vials (Schott, Stafford, Staffordshire, UK) prior to lyophilization. The lyophilization cycle parameters were as follows. Samples were frozen for 30 minutes at 5° C., 30 minutes at −5° C. and 60 minutes at −40° C., all at a ramp rate of 1.00° C./min. Primary drying was performed for 59 minutes at −37° C., 59 minutes at −28° C., 59 minutes at −23° C. and 552 minutes at −21° C., all at a ramp rate of 0.50° C./min. Secondary drying was performed at 20° C. for 360 minutes at a ramp rate of 0.10° C./min. All drying was performed with a chamber pressure of 57 mTorr. An alternate primary drying cycle was performed at 57 mTorr for 59 minutes at −38° C., 59 minutes at −38° C., 59 minutes at −37° C. and 552 minutes at −35° C., all at a ramp rate of 0.50° C./min. Lyophilized samples were sealed with 14 mm pharmaceutical grade butyl rubber freeze-dry stoppers (Fisher Scientific, Loughborough, Leicestershire, UK) and Parafilm M® (Sigma-Aldrich).

Lyoprotectants D-mannitol, D-(+)-glucose, D-(−)-fructose, sucrose, D-(+)-trehalose dihydrate (Sigma-Aldrich) or D(+)-mannose (Acros Organics) were solubilized in ddH$_2$O or PBS and added to liposome suspension to a final concentration of 2-4% w/v prior to lyophilization as indicated.

In the absence of sugars, ddH$_2$O- and PBS-rehydrated liposomes were ~210 nm before lyophilization. Without lyoprotectants, lyophilization increased liposome size by 3.55- and 6.05-fold in ddH$_2$O- and PBS-rehydrated samples, respectively. DCRL liposomes rehydrated in ddH$_2$O or PBS did not undergo significant size changes after addition of 3% sucrose, 4% mannitol or a combination, demonstrating that aggregation observed post-lyophilization was not caused directly by addition of the lyoprotectant(s).

For liposomes rehydrated in PBS, liposome size was significantly increased (2.00-fold) only in samples without lyoprotectant after the freeze cycle. However, after the full lyophilization cycle, liposome size was significantly increased 6.05-, 3.03-, 5.15- and 4.13-fold for samples without lyoprotectant, with 3% sucrose, with 4% mannitol and with a combination, respectively. Similarly, polydispersity was significantly increased by 2.61-, 2.61-, 2.85- and 2.79-fold for DCRL without lyoprotectant, with 3% sucrose, with 4% mannitol and with a combination, respectively, compared to pre-lyophilized controls.

For liposomes rehydrated in ddH$_2$O, vesicle size after the freeze cycle was increased significantly over pre-lyophilization controls by 17.90- and 11.45-fold for liposomes without lyoprotectants and with 4% mannitol, respectively, while liposomes with 3% sucrose or a combination of 3% sucrose and 4% mannitol underwent negligible changes. After the full lyophilization cycle, liposome sizes modestly changed 3.55-, 0.88-, 3.48- and 1.47-fold for samples without lyoprotectant, with 3% sucrose, with 4% mannitol and with a combination, respectively.

These findings demonstrate that liposomes rehydrated in ddH$_2$O have better colloidal stability in comparison to those rehydrated in PBS as illustrated by unchanged vesicle size post-lyophilization and that 3% sucrose may be a more ideal lyoprotectant for conferring good colloidal stability.

Toward the optimization of a lyophilization scheme for ddH$_2$O-rehydrated DCRL liposomes, the effect of 6 known sugar lyoprotectants (individually and in combination), at 2% w/v on vesicle size and polydispersity were evaluated.

Sucrose, glucose, mannitol, trehalose, fructose and mannose were tested as lyoprotectants. Only 2% mannitol as lyoprotectant significantly increased vesicle size (39.66-fold) and polydispersity (2.95-fold). However, while lyophilization with all other sugars did not result in appreciable size change, products lyoprotected with glucose, fructose and/or mannose collapsed into impermeable, compact layers of sugar and liposomes, which were difficult to rehydrate. Consistent with literature, liposomes lyoprotected with sucrose or trehalose prevented particle size change and resulted in a cake which could be reconstituted into a liposomal dispersion with good colloidal stability.

DCRL was also lyophilized with combinations of sugars. This study revealed that only 2% sucrose, 2% trehalose and 2% sucrose/2% trehalose supported good colloidal stability post-lyophilization and achieved pharmaceutically elegant cake structure. However, the combination of 2% sucrose/2% trehalose did not appear to be advantageous in terms of liposome size stability and polydispersity over lyoprotection with 2% sucrose or 2% trehalose alone.

Example 3—IBR/BVDV Vaccine

Quil A adjuvant has been reported to cause a systemic immune response often accompanied by a transient fever. Such fever is believed to be associated with milk yield drop in lactating cows. The objective of this study was to evaluate the effects of saponin-free liposomes on the immune response elicited by the liposomes and potential side effects caused by the adjuvants.

Eight-month old Holstein male calves were used for this study. Potential test animals were serologically screened and those with serum neutralization (SN) titers <1:2 for BVDV-1 and BVDV-2 were eligible for enrollment in the study. In addition, animals were not persistently infected (PI) with BVDV as determined by ear punch biopsy and immunohistochemistry. The animals were housed in environment controlled for temperature and humidity and received commercial deed and city-system water ad libitum.

Acclimation began about one week prior to study day 0. Calves received DRAXXIN® and DECTOMAX® prior to shipment.

Test animals that become moribund, injured, or died due to conditions unrelated to the investigation were excluded from the study and the relevant data analysis. Moribund animals were euthanized.

Animals were vaccinated on days zero and 28 by subcutaneous administration of 2 ml of the vaccine as summarized in Table 1.

TABLE 1

| | | VACCCINATION | |
|---|---|---|---|
| Grp | N | Vaccine | Adjuvant (per dose) |
| T01 | 9 | Saline | None |
| T02 | 9 | Quil A Containing Adjuvant + mBVDV ½ + mIBR | Quil A (250 µg), Cholesterol (250 µg), DDA (100 µg), CARBOPOL® (0.0375% v/v), BAYR1005® acetate (1,000 µg), CpG (SEQ ID NO: 8, 65% homogeneity, 100 µg) |
| T03 | 9 | DCRL + mBVDV ½ + mIBR | Liposomes containing Cholesterol (250 µg), DDA (250 µg), R1005 acetate (500 µg), Lecithin (500 µg) |
| T04 | 9 | DCRL-ORN (low) + mBVDV ½ + mIBR | DCRL liposomes as in T03, 25 µg ORN. |
| T05 | 9 | DCRL + CpG + ORN + mBVDV ½ + mIBR | DCRL liposomes as in T03, 100 µg ORN (SEQ ID NO: 11, with phosphorotioate bonds), CpG (SEQ ID NO: 8, 65% homogeneity). |
| T06 | 9 | DCRL-ORN (high) + mBVDV ½ + mIBR | DCRL liposomes as in T03, 100 µg SEQ ID NO: 11, with phosphorotioate bonds |
| T07 | 6 | Quil A Containing Adjuvant + BVDV1 r-gp53 | Adjuvant as in T02 |

On day 49, animals were challenged with Noncytopathic Bovine Viral Diarrhea Virus Type 2 (Strain 24515). Each animal received approximately 4.88 Log$_{10}$TCID$_{50}$ per dose in 5 ml administered intranasally (2.5 ml per nostril) using a compressed gas atomizer.

In groups T02-T06, the antigenic component contained 4500RUs/virus pre-inactivated modified BVDV ½ and modified IBR (8.0 log$_{10}$ TCID$_{50}$).

Animals were challenged on day 48 with 5 ml BVDV-2 strain 24515 (4.88 Log$_{10}$ TCID$_{50}$ per dose) intranasally (2.5 ml per nostril) using a compressed gas atomizer.

Rectal temperature least square means and ranges post-first and second vaccinations are shown in Table 2.

TABLE 2

Analysis of Least Squares Means for Rectal Temperatures Vaccination Phase

| | Time period, Day | | | | | | | | | |
|---|---|---|---|---|---|---|---|---|---|---|
| Grp | 0 | 1 | 2 | 3 | 7 | 28 | 29 | 30 | 31 | 35 |
| T01 | 102.4$^a$ | 102.0$^{ab}$ | 101.6$^a$ | 101.6$^a$ | 102.3$^a$ | 102.6$^{ab}$ | 101.9$^a$ | 101.8$^{ab}$ | 101.9$^b$ | 101.8$^a$ |
| T02 | 102.5$^a$ | 103.4$^c$ | 101.6$^a$ | 101.6$^a$ | 102.5$^a$ | 102.2$^{ab}$ | 103.4$^c$ | 102.2$^c$ | 101.8$^{ab}$ | 102.1$^b$ |
| T03 | 102.4$^a$ | 102.2$^{ab}$ | 101.7$^a$ | 101.5$^a$ | 102.2$^a$ | 102.4$^{ab}$ | 101.9$^a$ | 102.0$^{bc}$ | 101.8$^{ab}$ | 101.9$^{ab}$ |
| T04 | 102.5$^a$ | 102.0$^{ab}$ | 101.8$^a$ | 101.8$^a$ | 102.3$^a$ | 102.8$^b$ | 101.9$^a$ | 101.8$^{ab}$ | 101.8$^{ab}$ | 101.8$^a$ |
| T05 | 102.2$^a$ | 101.8$^a$ | 101.6$^a$ | 101.7$^a$ | 102.0$^a$ | 102.4$^{ab}$ | 102.0$^a$ | 101.8$^{ab}$ | 101.8$^{ab}$ | 101.8$^a$ |
| T06 | 102.1$^a$ | 102.0$^{ab}$ | 101.5$^a$ | 101.5$^a$ | 102.2$^a$ | 102.5$^{ab}$ | 101.8$^a$ | 101.6$^{ab}$ | 101.9$^b$ | 101.7$^a$ |
| T07 | 102.3$^a$ | 102.4$^b$ | 101.7$^a$ | 101.5$^a$ | 102.1$^a$ | 102.0$^a$ | 102.5$^b$ | 101.5$^a$ | 101.6$^a$ | 101.8$^a$ |

Values with different superscripts are significantly different (p ≤ 0.10)

The rectal temperatures for some T02 and T07 subjects showed a transient increase on day after both first and second vaccination. The increase in rectal temperatures of the animals in group T02 was significantly higher (P≤0.10) than in the other groups (T01, T03, T04, T05, T06, and T07) for 1 day post first vaccination.

After the first vaccination, four out of 9 animals in Group T02 had temperatures greater than 103.5° F. (three had temperatures of over 104.0° F.). In contrast, no animals in group T05 had temperatures over 102.5° F. one day after the first vaccination (data not shown).

After second vaccination increase in rectal temperatures of the T02 and T07 was significantly (P≤0.10) higher than the controls and vaccinates (T03, T04, T05, and T06), however, the elevated rectal temperatures were short lived (Table 2). Individual responses in group T02 ranged between 101.1 and 104.5° F. Five out of nine animals in Group T02 had temperatures over 103.5° F. (and another animal had temperature 103.5° F.) after the second vaccination. Only three out of nine animals in group T02 had temperature below 103.5° F. one day after the second vaccination. In contrast, none of the DCRL formulations induced an elevation of rectal temperatures greater than 103.7° F. Individual responses in Group T05 ranged between 101.4 and 102.6° F. (data not shown).

A febrile reaction was observed (>104.5° F.) in 8 of 8 animals in the T01 group post-challenge; this met the outcome criteria for a successful challenge. Rectal temperatures of all vaccinated groups were significantly lower (P≤0.10) on day 53 of study compared to the controls (4 days post-challenge) and there were some differences on subsequent days (data not shown). In the control group, in response to challenge, a typical biphasic elevation of the rectal temperature was observed.

The presence of clinical BVDV disease (an animal had to have a clinical score of ≥2) post-challenge was determined according to the following scoring system:

0—no clinical signs

1—Clinical signs as a whole are not specific for acute BVD infection. Clinical signs may include nasal discharge, abnormal respiration and mild lethargy.

2—Clinical signs as a whole are moderate in degree and specific for acute BVD infection. Clinical signs may include nasal discharge, abnormal respiration, lethargy, gauntness, ocular discharge, hypersalivation, diarrhea, dehydration, lameness and/or reluctance to move.

3—Clinical signs as a whole are severe in degree and characteristic for acute BVD infection. Clinical signs may include nasal discharge, abnormal respiration, lethargy, gauntness, ocular discharge, hypersalivation, diarrhea, excessive bruising, dehydration, recumbency, lameness and/or reluctance to move.

There were no significant differences between the control group and the vaccinated groups.

Leukopenia

The study outcome met the criteria for a valid study as 100% of T01 (controls) had leukopenia when using 40% drop and 75% of the controls had <4000 cells/μL. There were no significant differences between the number of animals that developed leukopenia≥40% decrease in white blood cells from background post-challenge in T01 compared with the vaccinated treatment groups T02, T03, T04, T05, T06, and T07 (P≤0.10). However, clinical leukopenia (<4000 cells/μL) which is a more relevant definition was detected in 6 of 8 (75%), 2 of 9 (22.2%), 1 of 8 (12.5%), 3 of 9 (33.3%), 4 of 9 (44.4%), 4 of 9 (44.4%), and 0 of 6 in T01, T02, T03, T04, T05, T06, and T07, respectively (Table 3). The duration of leukopenia was significantly longer (P≤0.10) in the T01 group when using≥40% drop compared to all vaccinates and significantly longer (P≤0.10) when using <4000 μl compared to the vaccinated groups T02, T03, T05, T06, and T07 (Table 4).

TABLE 3

Summary of Leukopenia Challenge Phase

| | Leukopenia (drop 40% or more) | | | | Leukopenia (<4000 cells per microliter) | | | |
|---|---|---|---|---|---|---|---|---|
| | No | | Yes | | No | | Yes | |
| Grp | N | % | N | % | N | % | N | % |
| T01 | 0 | 0 | 8 | 100 | 2 | 25 | 6 | 75 |
| T02 | 1 | 11.1 | 8 | 88.9 | 7 | 77.8 | 2 | 22.2 |
| T03 | 2 | 25 | 6 | 75 | 7 | 87.5 | 1 | 12.5 |
| T04 | 1 | 11.1 | 8 | 88.9 | 6 | 66.7 | 3 | 33.3 |
| T05 | 0 | 0 | 9 | 100 | 5 | 55.6 | 4 | 44.4 |
| T06 | 0 | 0 | 9 | 100 | 5 | 55.6 | 4 | 44.4 |
| T07 | 2 | 33.3 | 4 | 66.7 | 6 | 66.7 | 0 | 0 |

TABLE 4

Duration of Leukopenia

| | (drop 40% or more) | | | | <4000 cells per microliter | | | |
|---|---|---|---|---|---|---|---|---|
| Grp | LS mean days | Standard error | Lower 90% CI | Upper 90% CI | LS mean days | Standard error | Lower 90% CI | Upper 90% CI |
| T01 | 9.4$^a$ | 0.818 | 8 | 10.7 | 3.6$^a$ | 1.179 | 1.4 | 5.9 |
| T02 | 3.9$^{bc}$ | 0.771 | 2.6 | 5.2 | 0.7$^{bc}$ | 0.522 | −0.2 | 1.6 |
| T03 | 3.0$^{bc}$ | 0.818 | 1.6 | 4.4 | 0.1$^b$ | 0.095 | 0 | 0.3 |
| T04 | 3.4$^{bc}$ | 0.771 | 2.2 | 4.7 | 0.7$^{bc}$ | 0.522 | −0.2 | 1.6 |
| T05 | 4.4$^{bc}$ | 0.771 | 3.3 | 5.7 | 1.7$^{ac}$ | 0.799 | 0.2 | 3.2 |
| T06 | 4.6$^b$ | 0.771 | 3.3 | 5.8 | 1.1$^c$ | 0.522 | 0.2 | 2.0 |
| T07 | 2.5$^c$ | 0.944 | 0.90 | 4.1 | 0$^b$ | 0.11 | −0.2 | 0.2 |

Values with different superscripts are significantly different (p ≤ 0.10)

Viremia

All experimental vaccines protected against viremia. In some groups there was complete protection (T02 & T05 both containing CpG) and in others partial (T03, T04, T06, and T07). The number of viremic animals in T01 was significantly higher than the number in T02, T03, T04, T05, T06 and T07 (P≤0.10) (Table 5). No viremia was seen in the T02 and T05 groups. However, there was a difference between number of viremic animals in groups T03, T04, and T06 which contained no ORN, low dose ORN and high dose ORN when compared to the controls.

TABLE 5

Summary of Virus Isolation Challenge Phase

| | Sample Ever Positive | | | |
|---|---|---|---|---|
| | Yes | | No | |
| Grp | Number | % | Number | % |
| T01 | 0 | 0 | 8 | 100$^a$ |
| T02 | 9 | 100 | 0 | 0$^c$ |
| T03 | 6 | 75 | 2 | 25$^{bc}$ |
| T04 | 4 | 44.4 | 5 | 55.6$^b$ |
| T05 | 9 | 100 | 0 | 0$^c$ |
| T06 | 4 | 44.4 | 5 | 55.6$^b$ |
| T07 | 1 | 16.7 | 5 | 83.3$^{ab}$ |

Values with different superscripts are significantly different (p ≤ 0.10)

The duration of viremia for the T01 group was significantly greater than all the vaccinated groups (T02 through T07) (P≤0.1) (Table 6). Calves in T07 had received a vaccine containing a Quil A containing adjuvant+recombinant gp53 antigen of BVDV-1 virus and were also partially protected and had a significantly shorter duration of viremia compared with T01. For these calves the challenge was with a different biotype of BVDV (type 2) virus which reflects that there was partial cross-protection between the BVDV-1 gp53 antigen and the challenge strain.

TABLE 6

Days with positive virus shedding

| Grp | LS Mean days | Standard error | Lower 90% CI | Upper 90% CI |
|---|---|---|---|---|
| T01 | 8.1$^a$ | 0.451 | 7.4 | 8.9 |
| T02 | 0$^d$ | 0.168 | −0.3 | 0.3 |
| T03 | 0.4$^{cd}$ | 0.178 | 0.1 | 0.7 |
| T04 | 1.1$^{bc}$ | 0.426 | 0.4 | 1.8 |
| T05 | 0$^d$ | 0.168 | −0.3 | 0.3 |
| T06 | 0.7$^c$ | 0.168 | 0.4 | 0.9 |
| T07 | 2.2$^b$ | 0.521 | 1.3 | 3.0 |

Values with different superscripts are significantly different (p ≤ 0.10)

SN Titers

On Day 49, prior to challenge all T02 through T07 group animals had a SN titer to BVDV-1, BVDV-2 and only T02 through T06 had antibodies to IBR antigen of 1:8. All vaccines were considered to have adequate potency as they met the requirement of 1:8. The post first and second vaccination least square means of SN titers to BVDV-1 and 2 (Day 28 and 49) are shown in Table 7. All vaccinated animals had significantly higher SN titers than the control group and there were significant differences between SN titers of vaccinate groups. The liposomal vaccines (T03 though T06) induced significantly lower SN titers to BVDV-1 and 2 than the vaccine adjuvanted with a composition containing Quil A (T02). Addition of ORNS or CpG to these formulations did not enhance these responses. The gp53 vaccine adjuvanted with a composition containing Quil A also induced high SN titers by day 49 to the BVDV-1 antigen but lower to BVDV-2 antigen. The BVDV-1 SN titers of the T07 group were not significantly different from the titers of T02 but the BVDV-2 titers were. After the BVDV-2 challenge, the SN titers of all vaccinated groups were boosted whereas the T01 group calves developed primary antibody responses (day 63).

TABLE 7

Least Square Means BVDV-1a and BVDV2 SN titer

| | BVD-1a | | | | BVD-2 | | | |
|---|---|---|---|---|---|---|---|---|
| Grp | Day 0 | Day 28 | Day 29 | Day 63 | Day 0 | Day 28 | Day 29 | Day 63 |
| T01 | 1$^a$ | 1$^a$ | 1$^a$ | 11$^a$ | 1$^a$ | 1$^a$ | 1$^a$ | 450$^a$ |
| T02 | 1$^a$ | 29$^d$ | 1896$^c$ | 29193$^d$ | 1$^a$ | 25$^c$ | 878$^d$ | 96321$^e$ |
| T03 | 1$^a$ | 3$^b$ | 512$^b$ | 11337$^{bc}$ | 1$^a$ | 3$^b$ | 354$^c$ | 36521$^{cd}$ |
| T04 | 1$^a$ | 4$^{bc}$ | 621$^b$ | 8513$^b$ | 1$^a$ | 5$^b$ | 293$^c$ | 22292$^c$ |
| T05 | 1$^a$ | 7$^c$ | 492$^b$ | 22295$^{cd}$ | 1$^a$ | 7$^b$ | 376$^c$ | 53618$^d$ |
| T06 | 1$^a$ | 6$^{bc}$ | 767$^b$ | 15765$^c$ | 1$^a$ | 6$^b$ | 355$^c$ | 54058$^d$ |
| T07 | 1$^a$ | 6$^{bc}$ | 2814$^c$ | 35734$^d$ | 1$^a$ | 1$^a$ | 128$^b$ | 10624$^b$ |

Values with different superscripts are significantly different (p ≤ 0.10)

TABLE 8

Least Square Means IBR SN titer

| | IBR | | | |
|---|---|---|---|---|
| Grp | Day 0 | Day 28 | Day 29 | Day 63 |
| T01 | 1$^a$ | 1$^a$ | 1$^a$ | 1$^a$ |
| T02 | 1$^a$ | 9$^b$ | 149$^b$ | 94$^b$ |
| T03 | 1$^a$ | 2$^c$ | 21$^c$ | 15$^c$ |
| T04 | 1$^a$ | 3$^d$ | 24$^c$ | 15$^c$ |

TABLE 8-continued

Least Square Means IBR SN titer

| | IBR | | | |
|---|---|---|---|---|
| Grp | Day 0 | Day 28 | Day 29 | Day 63 |
| T05 | 1$^a$ | 3$^{cd}$ | 21$^c$ | 14$^c$ |
| T06 | 1$^a$ | 3$^{cd}$ | 19$^c$ | 13$^c$ |
| T07 | 1$^a$ | 1$^a$ | 1$^a$ | 1$^a$ |

Values with different superscripts are significantly different (p ≤ 0.10)

Injection Site Reactions

Least Squares means injection site reactions (ISR) for both left and right neck are shown in Tables 9 and 10. On Day 1, small reactions occurred in all six vaccination groups but receded. The largest reaction sites occurred in T02 and T07 on day 29, 41.8 and 16.3, respectively. There were significant differences between injection site reactions on certain days. All vaccines were safe as injection site reactions resolved rapidly.

TABLE 9

Least Squares mean for injection site reactions (Left Neck)

| | Left neck injection site reaction volume on day | | | | | | |
|---|---|---|---|---|---|---|---|
| Grp | 0 | 1 | 2 | 3 | 7 | 28 | 49 |
| T01 | −0.1$^a$ | −0.1$^a$ | −0.1$^a$ | −0.1$^a$ | −0.1$^a$ | −0.1$^a$ | −0.1$^a$ |
| T02 | 0.1$^a$ | 5.7$^b$ | 4.3$^{bc}$ | 7.9$^b$ | 10.4$^b$ | 1.3$^a$ | 0.2$^a$ |
| T03 | 0.0$^a$ | 3.0$^{ab}$ | 0.9$^{ab}$ | 0.7$^a$ | 1.5$^a$ | 0.0$^a$ | 0.0$^a$ |
| T04 | 0.1$^a$ | 0.6$^a$ | 2.1$^{abc}$ | 1.7$^a$ | 1.9$^a$ | 0.4$^a$ | 0.4$^a$ |
| T05 | −0.1$^a$ | 0.0$^a$ | 0.1$^a$ | 0.2$^a$ | 0.0$^a$ | −0.1$^a$ | −0.1$^a$ |
| T06 | 0.1$^a$ | 0.6$^a$ | 8.1$^d$ | 1.3$^a$ | 1.0$^a$ | 0.1$^a$ | 0.1$^a$ |
| T07 | 0.0$^a$ | 6.4$^b$ | 6.0$^{cd}$ | 9.8$^b$ | 2.7$^a$ | 0.3$^a$ | 1.1$^a$ |

Values with different superscripts are significantly different (p ≤ 0.10)

TABLE 10

Least Squares mean for injection site reactions (Right Neck)

| | Right neck injection site reaction volume on day | | | | | |
|---|---|---|---|---|---|---|
| Grp | 28 | 29 | 30 | 31 | 35 | 49 |
| T01 | 0.0$^a$ | 0.0$^a$ | 0.0$^a$ | 0.0$^a$ | 0.0$^a$ | 0.0$^a$ |
| T02 | 0.0$^a$ | 41.8$^c$ | 10.5$^b$ | 17.0$^c$ | 17.1$^b$ | 1.5$^a$ |
| T03 | 0.0$^a$ | 2.6$^a$ | 3.0$^a$ | 6.5$^{ab}$ | 5.2$^a$ | 0.0$^a$ |
| T04 | 0.0$^a$ | 3.8$^a$ | 1.1$^a$ | 1.8$^a$ | 1.3$^a$ | 0.4$^a$ |

TABLE 10-continued

Least Squares mean for injection site reactions (Right Neck)

| | Right neck injection site reaction volume on day | | | | | |
|---|---|---|---|---|---|---|
| Grp | 28 | 29 | 30 | 31 | 35 | 49 |
| T05 | 0.0$^a$ | 1.2$^a$ | 0.7$^a$ | 0.8$^a$ | 0.8$^a$ | 1.3$^a$ |
| T06 | 0.0$^a$ | 2.8$^a$ | 2.0$^a$ | 5.0$^{ab}$ | 3.2$^a$ | 0.8$^a$ |
| T07 | 0.0$^a$ | 16.3$^b$ | 5.6$^{ab}$ | 11.4$^{bc}$ | 5.8$^a$ | 0.0$^a$ |

Values with different superscripts are significantly different ($p \leq 0.10$)

Cell Mediated Immunity

The BVDV IFN gamma ELISPOT assay had a high background in the T01 group before challenge and hence, is considered unreliable for demonstration of induction of CMI responses by these vaccines to this antigen (data not shown). However the assays for the IBR antigens were reflective of induction of a CMI by the respective vaccines (see Tables 11-13, responses to killed IBR antigen, IBR gB and gD peptide recall responses of T02 through T06). In general the highest responses were in the T02 vaccine group and T05 group that had CpG in the formulation. Post-challenge responses were not enhanced as the challenge was a BVDV virus challenge. Presumably, similar CMI responses were induced by the vaccines to the BVDV antigen.

TABLE 11

| | IBR gB peptides IFN-gamma (SFC on day) | | | |
|---|---|---|---|---|
| Grp | 0 | 7 | 36 | 58 |
| T01 | 0.6$^a$ | 157.8$^b$ | 115.3$^a$ | 15.6$^a$ |
| T02 | 0.6$^a$ | 235.6$^b$ | 459.7$^{cd}$ | 215.3$^b$ |
| T03 | 4.1$^a$ | 280.0$^b$ | 518.8$^d$ | 141.3$^{ab}$ |
| T04 | 0.6$^a$ | 162.5$^b$ | 317.8$^b$ | 42.8$^a$ |
| T05 | 2.5$^a$ | 307.2$^b$ | 612.8$^d$ | 103.3$^{ab}$ |
| T06 | 1.9$^a$ | 274.4$^b$ | 328.9$^{bc}$ | 70.0$^{ab}$ |
| T07 | 1.3$^a$ | 82.9$^a$ | 97.1$^a$ | 28.8$^a$ |

Values with different superscripts are significantly different ($p \leq 0.10$)

TABLE 12

| | IBR gD peptides IFN-gamma (SFC on day) | | | |
|---|---|---|---|---|
| Grp | 0 | 7 | 36 | 58 |
| T01 | 0.0$^a$ | 127.8$^a$ | 135.3$^a$ | 11.3$^a$ |
| T02 | 1.1$^a$ | 209.2$^b$ | 562.2$^c$ | 127.2$^a$ |
| T03 | 1.3$^a$ | 150.0$^{ab}$ | 401.3$^{bc}$ | 117.8$^a$ |
| T04 | 1.7$^a$ | 139.7$^b$ | 301.1$^b$ | 76.1$^a$ |
| T05 | 2.8$^a$ | 244.2$^b$ | 402.2$^{bc}$ | 54.7$^a$ |
| T06 | 5.0$^a$ | 195.8$^b$ | 338.3$^b$ | 70.6$^a$ |
| T07 | 3.3$^a$ | 50.8$^a$ | 90.4$^a$ | 29.6$^a$ |

Values with different superscripts are significantly different ($p \leq 0.10$)

TABLE 13

| | mIBR antigen IFN-gamma (SFC on day) | | | |
|---|---|---|---|---|
| Grp | 0 | 7 | 36 | 58 |
| T01 | 5.6$^a$ | 199.7$^a$ | 210.6$^a$ | 15.6$^a$ |
| T02 | 0.8$^a$ | 591.9$^b$ | 1721.7$^c$ | 215.3$^a$ |
| T03 | 1.6$^a$ | 411.3$^{ab}$ | 1187.5$^b$ | 141.3$^a$ |
| T04 | 1.1$^a$ | 489.4$^b$ | 1340.8$^b$ | 42.8$^a$ |
| T05 | 1.4$^a$ | 643.9$^b$ | 1738.6$^c$ | 103.3$^a$ |
| T06 | 11.1$^a$ | 621.7$^b$ | 1129.2$^b$ | 70.0$^a$ |
| T07 | 2.5$^a$ | 106.3$^a$ | 328.3$^a$ | 28.8$^a$ |

Values with different superscripts are significantly different ($p \leq 0.10$)

A vaccine effect was observed on development and duration of viremia. All experimental vaccines protected against viremia. Complete protection was observed in some groups (T02 & T05 containing CpG) while partial protection was observed in the other groups (T03, T04, T06, and T07). The rectal temperature profiles showed a transient increase one day after both first and second vaccination for treatment groups T02 and T07 compared to T01 controls. Liposomal vaccines induced lower elevations in rectal temperature compared to T02 and T07 which had Quil A containing adjuvant. This Quil A containing adjuvant typically induces a single day elevation of temperature immediately after vaccination. The latter is particularly important for dairy cows because the fever accompanying the vaccination often results in an unacceptable milk yield drop. Liposomal formulations induced robust antibody as well as T cell responses (even Liposomes without additional immunomodulators). The Liposomal vaccines induced significantly lower SN titers to BVDV-1 and 2 and IBR antigen compared with the Quil A-containing vaccines although the levels reached were considered in the protective range for these respective diseases (BVDV-1 SN titers of 1:256-512; BVDV-2±256 or greater; IBR SN titer of 1:32).

In conclusion, the liposomal formulations offer a safe and new option to deliver killed antigens for diseases which require not only antibody but CMI as well for protection. The formulations were comparable to Quil-A containing vaccines in efficacy. CpG effect on efficacy was reproducible however the ORN was not effective in enhancing immunity against BVDV challenge.

Example 4—Swine Influenza Virus

The objective of this study was to evaluate immune response and efficacy of several SIV-vaccines (Killed Virus, pH1N1& H3N2) containing novel adjuvant formulations and immunomodulators. Efficacy was determined by both immunological parameters (humoral and cellular) and by efficacy endpoints including clinical signs, viremia, viral shedding and lung lesions.

Animals.

Three-week old (21+/−3 days) pigs of both sexes were used for this study. Animals had no history of exposure to PRRSV, Mycoplasma hyopneumoniae. Animals or their dams had no history of vaccination against or exposure to any SIV serotype. The animals arrived on site four to seven days prior to vaccination and were fed standard ration with water ad libitum.

The pigs were vaccinated with compositions of Table 14 on days zero (left neck) and 21 (right neck) and challenged with H3N2 virus IN/12 on day 35.

TABLE 14

Experimental setup

| Group | N | Antigen | Adjuvant | Dose/route |
|---|---|---|---|---|
| T01 | 10 | None | None | 2 ml IM |
| T02 | 10 | 80HA | 5% AMPHIGEN ® (lecithin oil emulsion) | 2 ml IM |
| T03 | 10 | pH1N1; 120HA | 20% AMPHIGEN ® + CpG (SEQ ID NO: 8, 50 µg/dose) + CD40 agonist (Anti-CD40 monoclonal antibody, Clone 2A5C7P1G8, 250 µg/dose) | 2 ml IM |
| T04 | 10 | H3N2 | 10% SP oil * | 2 ml IM |
| T05 | 10 | | 10% SP oil + CpG (SEQ ID NO: 8, 50 µg/dose) + CD40 agonist (250 µg/dose) | 2 ml IM |
| T06 | 10 | | TXO (CpG (SEQ ID NO: 8, 50 µg/dose + DEAE Dextran (10 mg/dose) + DRAKEOL ® 6VR (45% v/v), SPAN ®80 (6.3% v/v) + TWEEN ®80 (1.45% v/v) | 2 ml IM |
| T07 | 10 | | DCRL liposomes (Cholesterol (250 µg), DDA (250 µg), BAYR1005 ® acetate (500 µg), Lecithin (500 µg)) | 2 ml IM |

TABLE 14-continued

Experimental setup

| Group | N | Antigen | Adjuvant | Dose/route |
|---|---|---|---|---|
| T08 | 10 | | DCRL liposomes (Cholesterol (250 µg), DDA (250 µg), BAYR1005 ® free base(500 µg), Lecithin (500 µg)) + CpG (SEQ ID NO: 8, 50 µg/dose) + CD40 agonist (250 µg/dose) | 2 ml IM |

* 4% Squalane base subsolution diluted 10x for the final product (0.4% oil)

Blood serum was collected for hemagglutination inhibition (HAI) analysis on days 35 and 40, and whole blood collected for ELISPOT (IFNγ) analysis on days 28, 35, and 40. The pigs were sacrificed on day 40 (5 days post-challenge) and the percentage of consolidation for each lobe (left cranial, left middle, left caudal, right cranial, right middle, right caudal and accessory) was scored and recorded as a percentage between 0 and 100%.

None of the vaccinations resulted in systemic side effects or unacceptable injection side reactions (data not shown).

HAI titers are shown in Table 15.

TABLE 15

HI titers (Day 35-Pre-challenge, Day 40-post challenge)

| | CA09-H1N1 (vaccine #1) D 35 | | H3N2Vac (vaccine #2) D 35 | | H3N2v-IN/12 (challenge) D 35 | | H3N2v-IN/12 (challenge) D 40 | |
|---|---|---|---|---|---|---|---|---|
| Grp | Mean | SEM | Mean | SEM | Mean | SEM | Mean | SEM |
| T01 | 16.25$^a$ | 1.83 | 17$^a$ | 1.528 | <10 (nd) | na | 34$^a$ | 14.47 |
| T02 | 464$^b$ | 110.5 | 208$^b$ | 32 | 96 | 18.09 | 755.6$^b$ | 172.4 |
| T03 | 284$^b$ | 67.05 | 137.8$^b$ | 27.58 | 98 | 29.28 | 391.1$^b$ | 113.5 |
| T04 | 552$^b$ | 102.9 | 416$^b$ | 64 | 220 | 54.41 | 976$^b$ | 155.4 |
| T05 | 232$^b$ | 55.23 | 156$^b$ | 22.67 | 54 | 7.333 | 546$^b$ | 163.1 |
| T06 | 432$^b$ | 109.4 | 184$^b$ | 31.66 | 108 | 29.24 | 848$^b$ | 177 |
| T07 | 293.3$^b$ | 127.2 | 435.6$^b$ | 267.4 | 133.3 | 64.64 | 464$^b$ | 137.9 |
| T08 | 106.7$^b$ | 17.64 | 75.56$^b$ | 12.37 | 28.89 | 3.514 | 124$^b$ | 25.61 |

HU aValues with different superscripts are significantly different from T01 (p ≤ 0.10); Unpaired T test with Welch's correction (GraphPad Prism, Ver. 6.04).
nd, not detectable;
na, not applicable.

Lung Lesion scores are shown in table 16.

TABLE 16

Summary of lung lesion scores (Day 40)

| Grp | Mean | SEM | Lower 90% CI | Upper 90% CI | N |
|---|---|---|---|---|---|
| T01 | 3.029$^a$ | 0.8004 | 1.562 | 4.496 | 10 |
| T02 | 0.651$^b$ | 0.4224 | −0.1232 | 1.425 | 10 |
| T03 | 0.815$^b$ | 0.7331 | −0.5289 | 2.159 | 10 |
| T04 | 0.733$^b$ | 0.5106 | −0.203 | 1.669 | 10 |
| T05 | 1.36$^a$ | 0.7563 | −0.02643 | 2.746 | 10 |
| T06 | 0.237$^b$ | 0.1926 | −0.1161 | 0.5901 | 10 |
| T07 | 0.668$^b$ | 0.3254 | 0.07155 | 1.264 | 10 |
| T08 | 4.374$^a$ | 1.11 | 2.339 | 6.409 | 10 |
| NTX | 0.453$^b$ | 0.4161 | −0.3098 | 1.216 | 10 |

$^a$Values with different superscripts are significantly different from T01 (p ≤ 0.10); Unpaired T test with Welch's correction (GraphPad Prism, Ver. 6.04).
NTX is a group of unvaccinated, unchallenged pigs.

Group T04 had the highest HAI titer to one of the vaccine strains (H1N1), while T07 had the highest titer to the other strain (H3H2), even though, the titers in groups T02-T08 were significantly higher than in T01 control group.

All vaccines (except T08) tended to reduce LLS at 5 days post-challenge. Group T06 (TXO) tended to have the lowest Lung Lesion Scores.

Influenza NP protein peptide-specific IFN-gamma secreting cells and whole influenza virus-specific IFN-gamma secreting cells (both determined by ELISPOT) are provided in Tables 19 and 20, respectively. The peptides in the pools are 16-mers with a 12-amino acid overlap. The four pools contain sequence of NP peptide from N-terminus (Pool 1) to C-terminus (Pool 4). The sequences of the peptides are provided in tables 17 and 18.

TABLE 17

NP peptide pools used for IFN-γ ELISPOT (pools 1 and 2)

| NP peptide pool #1 | | NP peptide pool #2 | |
|---|---|---|---|
| SEQ ID NO: | Sequence | SEQ ID NO: | Sequence |
| 15 | MATQGTKRSYEQMETG | 45 | RQANNGEDATAGLTHI |
| 16 | GTKRSYEQMETGGERQ | 46 | NGEDATAGLTHIMIWH |
| 17 | SYEQMETGGERQDATE | 47 | ATAGLTHIMIWHSNLN |
| 18 | METGGERQDATEIKAS | 48 | LTHIMIWHSNLNDATY |
| 19 | GERQDATEIKASVGRM | 49 | MIWHSNLNDATYQRTR |
| 20 | DATEIKASVGRMVGGI | 50 | SNLNDATYQRTRALVR |
| 21 | IKASVGRMVGGIGRFY | 51 | DATYQRTRALVRTGMD |
| 22 | VGRMVGGIGRFYIQMC | 52 | QRTRALVRTGMDPRMC |
| 23 | VGGIGRFYIQMCTELK | 53 | ALVRTGMDPRMCSLMQ |
| 24 | GRFYIQMCTELKLSDY | 54 | TGMDPRMCSLMQGSTL |
| 25 | IQMCTELKLSDYEGRL | 55 | PRMCSLMQGSTLPRRS |

TABLE 17-continued

NP peptide pools used for IFN-γ ELISPOT (pools 1 and 2)

| NP peptide pool #1 | | NP peptide pool #2 | |
|---|---|---|---|
| SEQ ID NO: | Sequence | SEQ ID NO: | Sequence |
| 26 | TELKLSDYEGRLIQNS | 56 | SLMQGSTLPRRSGAAG |
| 27 | LSDYEGRLIQNSITIE | 57 | GSTLPRRSGAAGAAVK |
| 28 | EGRLIQNSITIERMVL | 58 | PRRSGAAGAAVKGVGT |
| 29 | IQNSITIERMVLSAFD | 59 | GAAGAAVKGVGTIAME |
| 30 | ITIERMVLSAFDERRN | 60 | AAVKGVGTIAMELIRM |
| 31 | RMVLSAFDERRNKYLE | 61 | GVGTIAMELIRMIKRG |
| 32 | SAFDERRNKYLEEHPS | 62 | IAMELIRMIKRGINDR |
| 33 | ERRNKYLEEHPSAGKD | 63 | LIRMIKRGINDRNFWR |
| 34 | KYLEEHPSAGKDPKKT | 64 | IKRGINDRNFWRGENG |
| 35 | EHPSAGKDPKKTGGPI | 65 | INDRNFWRGENGRRTR |
| 36 | AGKDPKKTGGPIYRRV | 66 | NFWRGENGRRTRAAYE |
| 37 | PKKTGGPIYRRVDGKW | 67 | GENGRRTRAAYERMCN |
| 38 | GGPIYRRVDGKWMREL | 68 | RRTRAAYERMCNILKG |
| 39 | YRRVDGKWMRELILYD | 69 | AAYERMCNILKGKFQT |
| 40 | DGKWMRELILYDKEEI | 70 | RMCNILKGKFQTAAQR |
| 41 | MRELILYDKEEIRRVW | 71 | ILKGKFQTAAQRAMMD |
| 42 | ILYDKEEIRRVWRQAN | 72 | KFQTAAQRAMMDQVRE |
| 43 | KEEIRRVWRQANNGED | 73 | AAQRAMMDQVRESRNP |
| 44 | RRVWRQANNGEDATAG | 74 | AMMDQVRESRNPGNAE |

TABLE 18

NP peptide pools used for IFN-γ ELISPOT (pools 3 and 4)

| NP peptide pool #3 | | NP peptide pool #4 | |
|---|---|---|---|
| SEQ ID NO: | Sequence | SEQ ID NO: | Sequence |
| 75 | QVRESRNPGNAEIEDL | 105 | RGVQIASNENVEAMDS |
| 76 | SRNPGNAEIEDLIFLA | 106 | IASNENVEAMDSNTLE |
| 77 | GNAEIEDLIFLARSAL | 107 | ENVEAMDSNTLELRSR |
| 78 | IEDLIFLARSALVLRG | 108 | AMDSNTLELRSRYWAI |
| 79 | IFLARSALVLRGSVAH | 109 | NTLELRSRYWAIRTRS |
| 80 | RSALVLRGSVAHKSCL | 110 | LRSRYWAIRTRSGGNT |
| 81 | VLRGSVAHKSCLPACV | 111 | YWAIRTRSGGNTNQQR |
| 82 | SVAHKSCLPACVYGLA | 112 | RTRSGGNTNQQRASAG |
| 83 | KSCLPACVYGLAVASG | 113 | GGNTNQQRASAGQISV |
| 84 | PACVYGLAVASGHDFE | 114 | NQQRASAGQISVQPTF |
| 85 | YGLAVASGHDFEREGY | 115 | ASAGQISVQPTFSVQR |
| 86 | VASGHDFEREGYSLVG | 116 | QISVQPTFSVQRNLPF |
| 87 | HDFEREGYSLVGIDPF | 117 | QPTFSVQRNLPFERAT |
| 88 | REGYSLVGIDPFKLLQ | 118 | SVQRNLPFERATIMAA |
| 89 | SLVGIDPFKLLQNSQV | 119 | NLPFERATIMAAFSGN |
| 90 | IDPFKLLQNSQVFSLI | 120 | ERATIMAAFSGNNEGR |
| 91 | KLLQNSQVFSLIRPNE | 121 | IMAAFSGNNEGRTSDM |
| 92 | NSQVFSLIRPNENPAH | 122 | FSGNNEGRTSDMRTEV |
| 93 | FSLIRPNENPAHKSQL | 123 | NEGRTSDMRTEVIRMM |
| 94 | RPNENPAHKSQLVWMA | 124 | TSDMRTEVIRMMESAK |
| 95 | NPAHKSQLVWMACHSA | 125 | RTEVIRMMESAKPEDL |
| 96 | KSQLVWMACHSAAFED | 126 | IRMMESAKPEDLSFQG |
| 97 | VWMACHSAAFEDLRVS | 127 | ESAKPEDLSFQGRGVF |
| 98 | CHSAAFEDLRVSSFIR | 128 | PEDLSFQGRGVFELSD |
| 99 | AFEDLRVSSFIRGKKV | 129 | SFQGRGVFELSDEKAT |
| 100 | LRVSSFIRGKKVIPRG | 130 | RGVFELSDEKATSPIV |
| 101 | SFIRGKKVIPRGKLST | 131 | ELSDEKATSPIVPSFD |
| 102 | GKKVIPRGKLSTRGVQ | 132 | EKATSPIVPSFDMSNE |
| 103 | IPRGKLSTRGVQIASN | 133 | SPIVPSFDMSNEGSYF |
| 104 | KLSTRGVQIASNENVE | 134 | PSFDMSNEGSYFFGDN |
| | | 135 | MSNEGSYFFGDNAEEY |
| | | 136 | GSYFFGDNAEEYDS |

TABLE 19

IFN-γ ELISPOT NP Peptide pools (Day 40)

| | NP peptide pool #1 | | NP peptide pool #2 | | NP peptide pool #3 | | NP peptide pool #4 | |
|---|---|---|---|---|---|---|---|---|
| Grp | Mean | Standard error | Mean | Standard error | Mean | Standard error | Mean | Standard error |
| T01 | 47[a] | 9.634 | 40[a] | 10.68 | 157[a] | 68.03 | 65.2[a] | 19.59 |
| T02 | 66[a] | 16.79 | 28.4[a] | 6.598 | 68.4[a] | 20.38 | 40.8[a] | 10.19 |
| T03 | 83[a] | 34.75 | 56.8[a] | 17.58 | 101.6[a] | 21.91 | 120[a] | 53.86 |

TABLE 19-continued

IFN-γ ELISPOT NP Peptide pools (Day 40)

| | NP peptide pool #1 | | NP peptide pool #2 | | NP peptide pool #3 | | NP peptide pool #4 | |
|---|---|---|---|---|---|---|---|---|
| Grp | Mean | Standard error | Mean | Standard error | Mean | Standard error | Mean | Standard error |
| T04 | 52.6$^a$ | 24.63 | 41.2$^a$ | 14.61 | 63$^a$ | 16.98 | 75.8$^a$ | 28.02 |
| T05 | 110.8$^b$ | 29.5 | 93.6$^b$ | 33.8 | 179.6$^a$ | 40.35 | 74$^a$ | 19.43 |
| T06 | 100.6$^a$ | 49.25 | 118.4$^a$ | 43.82 | 132.4$^a$ | 57.12 | 53.8$^a$ | 17.96 |
| T07 | 388.4$^b$ | 139.1 | 140.2$^b$ | 42.29 | 275.8$^a$ | 103.5 | 76.2$^a$ | 19.15 |
| T08 | 61.8$^a$ | 15.02 | 70.6$^a$ | 15.22 | 177.4$^a$ | 34.7 | 61.8$^a$ | 13.76 |

HU aValues with different superscripts are significantly different from T01 (p ≤ 0.10); Unpaired T test with Welch's correction (GraphPad Prism, Ver. 6.04).

NP protein is generally highly conserved among SIV strains, and therefore, an efficient CMI response likely translates into better cross-protection potential.

TABLE 20

IFN-γ ELISPOT virus recall antigen (Day 40)

| | H3N2v-IN/12 (challenge) | | CA09-H1N1 (vaccine #1) | | H3N2Vac (vaccine #2) | |
|---|---|---|---|---|---|---|
| Grp | Mean | Standard error | Mean | Standard error | Mean | Standard error |
| T01 | 91.8$^a$ | 25.4 | 30$^a$ | 10.56 | 23$^a$ | 5.41 |
| T02 | 216.6$^b$ | 36.69 | 147$^b$ | 16.6 | 312$^b$ | 75.42 |
| T03 | 387$^b$ | 72.43 | 231$^b$ | 40.74 | 497.4$^b$ | 84.63 |
| T04 | 390.8$^b$ | 65.18 | 225.6$^b$ | 41.22 | 513$^b$ | 108.3 |
| T05 | 524.4$^b$ | 80.27 | 255$^b$ | 52.56 | 598.2$^b$ | 87.71 |
| T06 | 419.6$^b$ | 108 | 584.2$^b$ | 149.6 | 491.2$^b$ | 144.9 |
| T07 | 788$^b$ | 164.7 | 552.8$^b$ | 115 | 1041$^b$ | 233.8 |
| T08 | 362$^b$ | 93.1 | 151.6$^b$ | 44.56 | 486.8$^b$ | 130.2 |

HU aValues with different superscripts are significantly different from T01 (p ≤ 0.10); Unpaired T test with Welch's correction (GraphPad Prism, Ver. 6.04).

Group T07 (DCRL liposomes) provided the highest IFN gamma responses to three of four NP protein peptide pools and two of the three whole viruses tested. The only group with observed post-vaccination (pre-challenge) IFN-γ response was T06 (TXO) (data not shown).

Adding CD40 agonist and CpG uniformly tended to decrease titers, as well as to increase LLS, especially in the context of the liposomal formulation.

Taken as a whole, these results indicate that the vaccine adjuvanted with DCRL liposomes is as effective as formulation T02 (experimental formulation similar to a commercial vaccine) in reducing lung lesion scores. At the same time, DCRL liposomes are much more effective in activating CMI response than the other vaccines tested, thus possibly providing a broader cross-protection potential and improved duration of immunity than the commercial product.

Example 5—Development of Immunity to *Eimeria maxima* Following Profilin Vaccination The objective of the study was to evaluate the effects of various adjuvants (Zoetic proprietary) on development of immunity to *Eimeria maxima* following profilin vaccination.

Newly hatched chicks were purchased from Longenecker's hatchery, Elizabethtown, Pa. Chicks were provided with feed and water ad libitum. Birds were kept in brooder pens in *Eimeria*-free facility and transferred into large hanging cages in a separate location where they were infected and kept until the end of experimental period.

Purified profilin (50 μg/dose) was mixed with different adjuvants as provided in Table 21.

TABLE 21

| Group | Vaccine composition |
|---|---|
| T01 | PBS |
| T02 | PBS |
| T03 | Profilin only (50 μg) |
| T04 | 50 μg profilin + 50 μg Cholesterol + CpG (SEQ ID NO: 8; 65% purity, 5 μg/ds) |
| T05 | 50 μg profilin + Quil-A (50 μg/dose), Cholesterol (50 μg/dose), CpG (5 μg/dose) |
| T06 | 50 μg profilin + Quil-A (50 μg/dose), Cholesterol (50 μg/dose), DDA (50 μg/dose), Carbopol (0.05%), BAYR1005 ® free base (100 μg/dose) |
| T07 | 50 μg profilin + Quil-A (50 μg/dose), Cholesterol (50 μg/dose), DDA (50 μg/dose), Carbopol (0.05%), BAYR1005 ® (100 μg/dose), CpG (SEQ ID NO: 8; 65% purity, 5 μg/ds) |
| T08 | 50 μg profilin + DCRL (Lyo) (DDA (12.5 μg/ds), Cholesterol (12.5 μg/ds), BAYR1005 ® (25 μg/ds), Lecithin (25 μg/ds)) |
| T09 | 50 μg profilin + DCRL + CpG (SEQ ID NO: 8; 65% purity, 5 μg/ds) (Lyo) (DDA (12.5 μg/ds), Cholesterol (12.5 μg/ds), BAYR1005 ® (25 μg/ds), Lecithin (25 μg/ds)) |
| T10 | 50 μg profilin + CpG (SEQ ID NO: 8; 65% purity, 25 μg/ds), DEAE-Dextran (500 μg/ds), 45% v/v Drakeol 6VR, Span-80 (6.3% v/v), Tween-80 (1.45% v/v) |

Birds were immunized with two subcutaneous injections (0.5 mL per dose) of profilin plus adjuvant at day 1 and day 7 of age subsequently. Seven days following second immunization (14 days of age), birds (Except in group T01) were challenged with 1×10$^4$ sporulated oocysts of *Eimeria maxima*.

Body weight gain was determined on d 6 and d 15 following challenge. Oocysts shed in the feces from day 6-9 following challenge was also determined. Serum antibodies against profilin were evaluated by ELISA.

Control groups: PBS injections and no challenge (non-vaccinated unchallenged control), PBS injections and challenge on d 14 (non-vaccinated challenged control), profilin/no adjuvant and challenge on d 14 (Antigen control).

To assess lesion scores, six birds/group were killed 6 d post challenge. Approximately 20 cm intestinal segments extending 10 cm anterior and posterior to diverticulum were obtained and cut longitudinally. Intestinal contents were removed gently. A score ranging from 0-4 was given depending on the severity of lesions.

To assess fecal oocyst production, feces from each group (8 birds/group; 4 cages with 2 birds/cage) were collected separately from 6 to 9 days post challenge. Starting from 6 days post challenge, collection cages were set up and animal caretakers were instructed not to clean the feces. Fecal droppings were collected from each oocyst collecting cage that holds 2 birds per cage. Collecting pans were placed under each cage for 3 days starting from 6 days pi, and fecal material was collected into large plastic jars. Fecal droppings in each jar were ground in a blender with water, and two 35 ml random samples were taken from each sample. In order to count coccidia oocysts, various dilutions were made initially to determine the optimum dilutions for enumeration of oocysts for each sample. Oocysts were counted microscopically. The total number of oocysts shed per chicken was calculated using the formula: total oocysts/bird=(oocyst count×dilution factor×fecal sample volume/counting chamber volume)/number of birds per cage.

Blood samples (4 birds/group) were collected on day 9 post Eimeria challenge for antibody response measurements. Blood samples were allowed to clot at 4° C. for 4 hr, and the sera separated. Serum samples were tested for antibodies against Eimeria using ELISA. Briefly, microtiter plates were coated overnight with 200 ng/well of the recombinant coccidial antigen, washed with PBS-0.05% Tween, and blocked with PBS-1% BSA. Serum dilutions were added, incubated with continuous gentle shaking, washed, and bound Ab detected with peroxidase-conjugated rabbit anti-chicken IgG (Sigma) and peroxidase-specific substrate. Optical density (OD) was measured at 450 nm with a microplate reader (Bio-Rad, Richmond, Calif.).

All values are expressed as mean±SEM. Differences among means were considered significant at $p<0.05$.

The negative control and challenge control were significantly different at 6 days but not 15 days post-infection. Day 6 post-challenge weight loss in challenge controls as compared to negative controls was about 15%. No treatment differed from no adjuvant or challenge controls but treatments T05, T06, and T08 did not differ from the negative control either.

Just under 60% of the birds had lesion scores of 2 or higher. No formulations were significantly different from the challenge control. Group T09 was the poorest performer. T04 was the best performer.

Generally speaking a decrease of <1 log in output is not considered biologically relevant, but can still be indicative of active immunity. Only formulations that were significantly less than the challenge control were T05 and T09.

Antibody response is not generally considered relevant to immunity to coccidiosis so may not correlate to other criteria. In the experiments above, group T07 elicited antibody response which was higher than the responses elicited either by negative (unvaccinated, uninfected birds), the positive control (non-vaccinated, infected birds), or the birds vaccinated with the antigen only. Groups T05, T06, and T08-T10 elicited antibody responses higher than the negative control (unvaccinated, uninfected birds).

The results are summarized in Table 22. Weight gain, serum antibody levels (expressed as a % of uninfected control) and lesion scores, oocyst production (expressed as a % of infected control) following immunization of birds with two subcutaneous injections of profilin plus various adjuvants at day 1 and day 7 of age and subsequent challenge with $1×10^4$ oocysts of Eimeria maxima at 14 days of age.

TABLE 22

| Grp | Weight gain, % of control Day 0-6 | Weight gain, % of control Day 0-15 | Oocyst production, % of infected control, day 6 | Lesion score, % of infected control, day 6 | Serum AB titer (OD450), % of control |
|---|---|---|---|---|---|
| T01 | 100 | 100 | 0 | 0 | 100 |
| T02 | 85 | 96 | 100 | 100 | 189 |
| T03 | 86 | 96 | 83 | 63 | 193 |
| T04 | 93 | 95 | 117 | 63 | 194 |
| T05 | 88 | 87 | 63 | 53 | 231 |
| T06 | 83 | 90 | 74 | 74 | 268 |
| T07 | 92 | 96 | 83 | 42 | 310 |
| T08 | 81 | 88 | 108 | 74 | 203 |
| T09 | 86 | 95 | 56 | 95 | 205 |
| T10 | 86 | 87 | 113 | 63 | 269 |

Example 6—BVDV/IBR Vaccine Adjuvanted with DCRL+CpG

In this example, adjuvanting potential of DCRL liposomes with CpG (without ORN) was accessed. In addition, different methods of loading the liposomes were compared.

The experimental setup was as follows (Table 21):

| Trmt Group | N | Treatment | Adjuvant (per Dose) |
|---|---|---|---|
| T01 | 9 | Saline Negative Control | |
| T02 | 9 | Quil A containing adjuvant (gp53 from BVDV 1 and BVDV 2) | Quil-A (250 µg), Cholesterol (250 µg), DDA (100 µg), CARBOPOL ® (0.0375% v/v), BAYR1005 ®acetate (1,000 µg), SEQ ID NO: 8 (100 µg, 65% homogeneous) + 10 µg each of recombinant BVDV 1 and 2 gp 53 |
| T03 | 9 | DCRL + T (sucrose lyoph. without antigen) + mBVDV 1, mBVDV 2 & mIBR | Cholesterol (250 µg), DDA (250 µg), BAYR1005 ® free base (500 µg), Lecithin (500 µg), SEQ ID NO: 8 (100 µg, 65% homogeneous) |
| T04 | 9 | DCRL + T (not lyoph) mBVDV 1, mBVDV 2 & mIBR | As in T03 |
| T05 | 9 | DCRL + T (active load with antigen then sucrose lyoph) mBVDV 1, mBVDV 2 & mIBR | As in T03 |
| T06 | 9 | DCRL-ORN (sucrose lyoph) mBVDV 1, mBVDV 2 & mIBR | Cholesterol (250 µg), DDA (250 µg), BAYR1005 ® free base (500 µg), Lecithin (500 µg), SEQ ID NO: 11, with phosphorotioate bonds (100 µg) |

Vaccines in groups T03-T06 also contained mBVD1 (4,500 RU/ds)+BVDV1 (4500RUs), BVDV 2 (4500RUs), mIBR $10^8$ $\log_{10}$ $TCID_{50}$ (pre-inactivation dose).

Healthy Holstein calves (6-7 months old, seronegative for BVDV1, BVDV2 and IBR) were enrolled in this study (n=9/treatment group). Calves were administered 2 mL of the assigned vaccine subcutaneously on Days 0 and 28. A virulent BVDV2 challenge (4 mL (5.14 $Log_{10}$ $TCID_{50}$ per dose) intranasally) was administered on Day 49. Clinical observations were performed and injection sites and rectal temperatures were measured around each vaccination. Blood samples were collected for white blood cell counts, viremia and serology through Day 63.

All calves in T02, T03, T04 and T06 achieved 1:8 titers against BVDV-1a and BVDV2 before challenge, compared to 22.1 and 11.1% of the calves in T05. It is believed that due to active loading used in T5, the majority of the antigen was removed from the vaccine preparation. As such, the animals in group T05 received less antigen than the animals in groups T03, T04, and T06. Therefore, the interpretation of the findings from group T05 should be interpreted cautiously.

That being said, the BVDV-1a and BVDV2 titers for T05 were significantly lower than the other vaccinated groups in Days 28, 49 and 63. No calves in T02 or T05 achieved 1:8 titers against BHV before challenge, and these groups also had significantly lower titers compared to the other vaccinated groups on Days 28, 49 and 63. The Least Square Mean for gp53-1 SFC was significantly higher for T02 compared to all other treatment groups on Days 0, 35 and 56, and the Lease Square Means for gp53-2 SFC was significantly higher for T02 on Days 35 and 56.

Viremia was observed in all calves in T01 and T05. No calves in T02 developed viremia following challenge. In groups T03, T04 and T06, 22.2, 33.3 and 33.3% of the calves developed viremia; these groups were not significantly different from T02. The duration of viremia was significantly longer in T01 and T05 compared to all other treatment group. When leukopenia was determined by a 40% reduction in WBC from baseline, 22.2% of the calves in T02 were leukopenic after challenge, while all calves in all groups were leukopenic. Calves in T01 and T05 had significantly longer duration of leukopenia compared to all other groups (8.6 days, zero days, 0.2 days, 0.7 days, 6.7 days, and 0.8 days for groups T01-T06, respectively). Only mild signs of clinical disease were observed following challenge in this study. In the T01 control group, 22.2% of the calves had clinical scores of ≥2 after challenge, while 11.1% of the calves in T05 had clinical scores of ≥2 after challenge. No calves in any other treatment group had clinical scores of ≥2 after challenge.

Transient fevers were observed in T02 on Days 1 and 29. The temperatures of all other calves were normal throughout the study.

TABLE 22

LSMeans for Vaccination Phase Rectal Temperature, ° F.

| Trt. | Day 00 | Day 01 | Day 02 | Day 03 | Day 07 | Day 28 | Day 29 | Day 30 | Day 31 | Day 35 |
|---|---|---|---|---|---|---|---|---|---|---|
| T01 | 102.1$^{ab}$ | 101.9$^a$ | 101.9$^a$ | 101.9$^a$ | 102.0$^a$ | 101.9$^{ab}$ | 102.1$^a$ | 102.0$^a$ | 102.0$^a$ | 102.3$^a$ |
| T02 | 101.9$^a$ | 103.1$^b$ | 101.7$^a$ | 101.9$^a$ | 102.0$^a$ | 101.9$^{ab}$ | 103.2$^b$ | 102.3$^a$ | 102.1$^{ab}$ | 102.2$^a$ |
| T03 | 101.9$^a$ | 102.1$^a$ | 101.7$^a$ | 102.0$^a$ | 102.3$^{ab}$ | 101.7$^a$ | 102.1$^a$ | 102.1$^a$ | 102.1$^{ab}$ | 102.1$^a$ |
| T04 | 101.9$^a$ | 101.9$^a$ | 101.7$^a$ | 101.9$^a$ | 102.3$^{ab}$ | 102.2$^b$ | 102.4$^a$ | 102.3$^a$ | 102.3$^b$ | 102.4$^a$ |
| T05 | 102.1$^{ab}$ | 102.0$^a$ | 101.9$^a$ | 102.3$^a$ | 102.5$^b$ | 102.0$^{ab}$ | 102.2$^a$ | 102.0$^a$ | 102.2$^{ab}$ | 102.1$^a$ |
| T06 | 102.3$^b$ | 102.1$^a$ | 101.7$^a$ | 102.0$^a$ | 102.1$^{ab}$ | 101.8$^a$ | 102.3$^a$ | 102.0$^a$ | 102.1$^{ab}$ | 102.2$^a$ |

Values with different superscripts are significantly different (p ≤ 0.10)

TABLE 23

LSMeans for Challenge Phase Rectal Temperature, ° F.

| Trt. | Day 47 | Day 48 | Day 49 | Day 50 | Day 51 | Day 52 | Day 53 | Day 54 | Day 55 |
|---|---|---|---|---|---|---|---|---|---|
| T01 | 102.3$^a$ | 101.9$^a$ | 101.7$^a$ | 101.8$^a$ | 101.7$^a$ | 101.9$^a$ | 102.6$^{de}$ | 102.5$^b$ | 102.4$^b$ |
| T02 | 102.3$^{ac}$ | 101.9$^a$ | 101.7$^a$ | 101.7$^a$ | 102.1$^{bc}$ | 101.9$^a$ | 101.6$^a$ | 101.9$^a$ | 101.9$^a$ |
| T03 | 102.3$^{ab}$ | 101.8$^a$ | 102.1$^{ab}$ | 101.8$^a$ | 102.1$^{bc}$ | 101.9$^a$ | 102.1$^{bc}$ | 102.7$^b$ | 102.6$^b$ |
| T04 | 102.5$^{bc}$ | 102.0$^a$ | 102.3$^b$ | 101.8$^a$ | 102.3$^c$ | 101.9$^a$ | 101.9$^b$ | 102.4$^b$ | 102.1$^{ab}$ |
| T05 | 102.4$^{ac}$ | 101.9$^a$ | 101.8$^{ab}$ | 102.0$^a$ | 101.8$^{ab}$ | 102.0$^a$ | 103.0$^e$ | 102.7$^b$ | 102.4$^b$ |
| T06 | 102.3$^{ab}$ | 102.0$^a$ | 101.9$^{ab}$ | 101.7$^a$ | 102.1$^{bc}$ | 101.9$^a$ | 102.3$^{cd}$ | 102.4$^b$ | 102.1$^{ab}$ |

| Trt. | Day 56 | Day 57 | Day 58 | Day 59 | Day 60 | Day 61 | Day 62 | Day 63 |
|---|---|---|---|---|---|---|---|---|
| T01 | 102.6$^b$ | 103.5$^b$ | 104.5$^{cd}$ | 105.2$^d$ | 104.5$^{bc}$ | 103.8$^b$ | 103.2$^b$ | 102.5$^b$ |
| T02 | 101.8$^a$ | 102.5$^a$ | 102.3$^a$ | 102.5$^a$ | 102.5$^a$ | 102.4$^a$ | 101.5$^a$ | 101.8$^{ab}$ |
| T03 | 102.6$^{ab}$ | 103.4$^{ab}$ | 103.7$^{bc}$ | 103.5$^{ab}$ | 102.6$^a$ | 102.0$^a$ | 101.6$^a$ | 102.1$^{ab}$ |
| T04 | 102.8$^b$ | 102.9$^{ab}$ | 103.3$^b$ | 104.9$^{cd}$ | 103.8$^{ab}$ | 102.6$^a$ | 101.6$^a$ | 101.7$^a$ |
| T05 | 102.9$^b$ | 104.6$^c$ | 105.0$^d$ | 105.2$^d$ | 105.3$^c$ | 104.3$^b$ | 102.6$^b$ | 102.4$^{ab}$ |
| T06 | 102.4$^b$ | 102.8$^a$ | 103.2$^b$ | 104.2$^{bc}$ | 103.0$^a$ | 102.0$^a$ | 101.6$^a$ | 101.7$^a$ |

Values with different superscripts are significantly different (p ≤ 0.10)

Analysis of individual animals revealed that in group T02 (adjuvanted with a Quil A containing adjuvant), four animals had temperature over 103.5F after the first injection and two animals had temperature over 103.5 F after the second injection. In addition, one animal had temperature 103.2 F on day 1 (a day after the first vaccination) and five had temperatures in range of 103.0-103.4 F on day 29 (a day after the second vaccination). In contrast, none of the animals vaccinated with the adjuvants lacking Quil A had temperatures over 103.5 F either after the first or after the second vaccination. Two had temperatures in the range of 103.0-103.4 F.

No injection site reactions>200 cm$^3$ were observed in this study. Group T02 (adjuvanted with a Quil A—containing adjuvant) had significantly larger injection site reactions on Day 2, 7 and 29 compared to all other treatment groups. Measurable injection site reactions were still present on Day 49 in T02 (second injection) and T06 (first injection).

TABLE 24

LSMeans for Injection Site Reactions following First Vaccination (cm$^3$)

| Treatment | Day 00 | Day 01 | Day 02 | Day 03 | Day 07 | Day 28 | Day 49 |
|---|---|---|---|---|---|---|---|
| T01 | 0.0$^a$ | 0.0$^a$ | 0.0$^a$ | 0.0$^a$ | 0.0$^a$ | 0.0$^a$ | 0.0$^a$ |
| T02 | 0.0$^a$ | 2.0$^a$ | 5.4$^c$ | 5.7$^b$ | 7.2$^c$ | 0.2$^a$ | 0.0$^a$ |
| T03 | 0.0$^a$ | 0.3$^a$ | 1.8$^{ab}$ | 1.2$^a$ | 1.0$^{ab}$ | 0.0$^a$ | 0.0$^a$ |
| T04 | 0.0$^a$ | 0.4$^a$ | 2.1$^b$ | 0.0$^a$ | 2.0$^{ab}$ | 0.0$^a$ | 0.0$^a$ |
| T05 | 0.0$^a$ | 0.0$^a$ | 0.0$^a$ | 0.0$^a$ | 0.0$^a$ | 0.0$^a$ | 0.0$^a$ |
| T06 | 0.0$^a$ | 1.2$^a$ | 3.3$^b$ | 4.2$^b$ | 2.1$^b$ | 0.0$^a$ | 0.6$^a$ |

Values with different superscripts are significantly different (p ≤ 0.10)

TABLE 25

LSMeans for Injection Site Reactions following Second Vaccination (cm$^3$)

| Treatment | Day 28 | Day 29 | Day 30 | Day 31 | Day 35 | Day 49 |
|---|---|---|---|---|---|---|
| T01 | 0.0$^a$ | 0.0$^a$ | 0.0$^a$ | 0.3$^a$ | 0.0$^a$ | 0.0$^a$ |
| T02 | 0.0$^a$ | 35.8$^b$ | 5.8$^b$ | 5.4$^a$ | 8.3$^{bc}$ | 0.2$^a$ |
| T03 | 0.0$^a$ | 2.4$^a$ | 0.4$^{ab}$ | 3.6$^a$ | 9.8$^c$ | 0.0$^a$ |
| T04 | 0.0$^a$ | 0.9$^a$ | 1.2$^{ab}$ | 5.1$^a$ | 1.9$^a$ | 0.0$^a$ |
| T05 | 0.0$^a$ | 0.0$^a$ | 0.0$^a$ | 0.0$^a$ | 0.0$^a$ | 0.0$^a$ |
| T06 | 0.0$^a$ | 1.2$^a$ | 1.2$^{ab}$ | 3.0$^a$ | 3.9$^{ab}$ | 0.0$^a$ |

Values with different superscripts are significantly different (p ≤ 0.10)

In sum, vaccine candidates T02, T03, T04 and T06 met the outcome criteria for providing BVDV2 titers>1:8 in all calves. Vaccine candidate T02 also provided 100% protection against viremia and complete protection against leukopenia (as measured by 40% reduction in WBC). Calves in this group experienced transient fever and injection site reactions.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. An essentially saponin-free liposome, wherein said saponin is absent or present at or below the limit of detection, comprising an external lipid bilayer membrane and an internal compartment, the external membrane comprising:
   a) a quaternary ammonium compound composed of four alkyl chains, two of which are $C_{10}$-$C_{20}$ alkyls and the remaining two are $C_1$-$C_4$ alkyls;
   b) a sterol selected from the group consisting of β-sitosterol, stigmasterol, ergosterol, ergocalciferol, and cholesterol;
   c) a phospholipid; and
   d) a glycolipid of formula I:

Formula I $$R^5-O-CH_2$$
$$R^4-O \cdots O \cdots CO-X-R^2$$
$$R^3-O \cdots NH-R^6 \quad N-R^1$$

wherein, $R^1$ and $R^2$ are independently hydrogen, or a saturated alkyl radical having up to 20 carbon atoms; X is $-CH_2-$, $-O-$ or $-NH-$; $R^2$ is hydrogen, or a saturated alkyl radical having up to 20 carbon atoms; $R^3$, $R^4$, and $R^5$ are independently hydrogen, $-SO_4^{2-}$, $-PO_4^{2-}$, $-COC_{1-10}$ alkyl; $R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers.

2. The liposome of claim 1, wherein said liposome is saponin-free.

3. The liposome of claim 1, wherein the quaternary ammonium compound is DDA, the sterol is cholesterol, and the glycolipid is N-(2-Deoxy-2-L-leucylamino-β-D-glucopyranosyl)-N-octadecyldodecanoylamide or a salt thereof.

4. The liposome of claim 1, further comprising an immunostimulatory oligonucleotide selected from the group consisting of an immunostimulatory ribonucleotide, a CpG oligodeoxyribonucleotide, and a combination thereof.

5. The liposome of claim 4, wherein said immunostimulatory oligonucleotide comprises any one of SEQ ID NOs 1-14.

6. An adjuvant formulation comprising the liposome according to claim 1, wherein in said adjuvant formulation saponin is absent or present at or below the limit of detection.

7. The adjuvant composition of claim 6, wherein said adjuvant formulation is saponin-free.

8. A vaccine composition comprising an effective amount of an antigenic component and an immunologically effective amount of the adjuvant formulation of claim 6, wherein in said vaccine composition saponin is absent or present at or below the limit of detection.

9. The vaccine composition of claim 8, wherein said vaccine composition is saponin-free.

10. The vaccine composition of claim 8, wherein the antigenic component comprises IBR, BVDV-1, and BVDV-2.

11. A method of inducing an immune response against BVDV in a bovine comprising administered to said bovine the vaccine composition according to claim 10.

12. The method of claim 11, wherein said immune response is induced without an accompanying fever.

13. The vaccine composition of claim 8, wherein the antigenic component is selected from the group consisting of bovine antigens, caprine antigens, porcine antigens, poultry antigens, equine antigens, canine antigens, equine antigens and feline antigens.

14. The vaccine composition of claim 13, wherein the antigenic component comprises an ssRNA virus, and wherein the vaccine composition is substantially free of CpG oligodeoxyribonucleotide.

15. The vaccine of claim 14, wherein the ssRNA virus is an influenza virus.

16. The vaccine of claim 15, wherein the influenza virus is an inactivated Swine Influenza Virus (SIV).

17. The vaccine composition of claim 8, wherein the immunostimulatory oligonucleotide comprises a CpG oligodeoxyribonucleotide.

18. The vaccine composition of claim 17, wherein the antigen comprises a poultry antigen.

19. The vaccine composition of claim 18, wherein the antigen is profilin.

20. A method of prevention of *Eimeria* oocyst shedding in a poultry animal infected with *Eimeria*, comprising administering to said animal the vaccine composition of claim 19 prior to said infection.

21. A method of preparing the liposome of claim 1, the method comprising:
   a) dissolving in an organic solvent the quaternary ammonium compound, the sterol, the phospholipid, and the glycolipid of formula I:

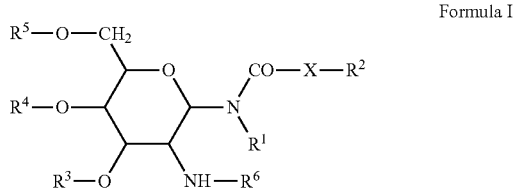

Formula I wherein, $R^1$ and $R^2$ are independently hydrogen, or a saturated alkyl radical having up to 20 carbon atoms; X is —$CH_2$—, —O— or —NH—; $R^2$ is hydrogen, or a saturated alkyl radical having up to 20 carbon atoms; $R^3$, $R^4$, and $R^5$ are independently hydrogen, —$SO_4^{2-}$, —$PO_4^{2-}$, —$COC_{1-10}$ alkyl; $R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers;
   b) removing the organic solvent and forming a film;
   c) rehydrating the film in an aqueous solvent thereby forming a rehydrated composition;
   d) microfluidizing the rehydrated composition.

22. The method of claim 21, wherein the aqueous solvent comprises an immunostimulatory oligonucleotide.

23. The essentially saponin-free liposome according to claim 1, wherein the weight ratios of the quaternary ammonium compound: the sterol: the phospholipid: the glycolipid are 1:0.75-1.25:1.5-2.5:1.5-2.5, respectively.

24. The essentially saponin-free liposome according to claim 23, wherein the weight ratios of the quaternary ammonium compound: the sterol: the phospholipid: the glycolipid are 1:1:2:2.

25. The essentially saponin-free liposome according to claim 1, wherein
   a) the total weight of the quaternary ammonium compound and the sterol is about 10-60% of the total weight of the glycolipid and the phospholipid;
   b) the quaternary ammonium compound comprises at least about 5% w/w of the total weight of the quaternary ammonium compound, the sterol, the phospholipid, and the glycolipid; and
   c) the glycolipid is at least about 20% w/w of the total weight of the quaternary ammonium compound, the sterol, the phospholipid, and the glycolipid.

* * * * *